(12) United States Patent
Miki

(10) Patent No.: US 12,422,665 B2
(45) Date of Patent: Sep. 23, 2025

(54) OPTICAL UNIT, FIBER SCANNING DEVICE, AND METHOD FOR MANUFACTURING OPTICAL UNIT

(71) Applicant: OLYMPUS CORPORATION, Tokyo (JP)

(72) Inventor: Takehiro Miki, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 363 days.

(21) Appl. No.: 18/081,135

(22) Filed: Dec. 14, 2022

(65) Prior Publication Data

US 2023/0124065 A1 Apr. 20, 2023

Related U.S. Application Data

(63) Continuation of application No. PCT/JP2020/024216, filed on Jun. 19, 2020.

(51) Int. Cl.
*G02B 23/26* (2006.01)
*A61B 1/00* (2006.01)
(Continued)

(52) U.S. Cl.
CPC ............ *G02B 23/26* (2013.01); *A61B 1/0011* (2013.01); *A61B 1/0676* (2013.01); *G02B 7/02* (2013.01);
(Continued)

(58) Field of Classification Search
None
See application file for complete search history.

(56) References Cited

U.S. PATENT DOCUMENTS

| 786,052 A | * | 3/1905 | Roebuck | ........... | G02B 7/02 |
| | | | | | 353/100 |
| 859,215 A | * | 7/1907 | Guilbert | ........... | G02B 7/02 |
| | | | | | 359/819 |

(Continued)

FOREIGN PATENT DOCUMENTS

| CA | 2667803 A1 | 7/2008 |
| JP | 2008170797 A | 7/2008 |

(Continued)

OTHER PUBLICATIONS

International Search Report dated Sep. 1, 2020 issued in PCT/JP2020/024216.

*Primary Examiner* — Jerry Rahll
(74) *Attorney, Agent, or Firm* — Scully, Scott, Murphy & Presser, P.C.

(57) ABSTRACT

An optical unit includes a first lens, a second lens, and a holding member. The first lens is formed in a spherical segment having a first flat surface and a first convex spherical surface. The second lens is formed in a spherical segment having a second flat surface and a second convex spherical surface. A holding member has a first end portion that surrounds the first lens and a second end portion that surrounds the second lens. The holding member holds the first lens and the second lens with a frictional force such that the first convex spherical surface and the second convex spherical surface are adjacent to each other between the first end portion and the second end portion. The first end portion is located on the same surface as the first flat surface or closer to the second lens than the first flat surface. The second end portion is located on the same surface as the second flat surface or closer to the first lens than the second flat surface.

19 Claims, 16 Drawing Sheets

(51) Int. Cl.
*A61B 1/06* (2006.01)
*G02B 7/02* (2021.01)
*G02B 13/00* (2006.01)
*G02B 23/24* (2006.01)

(52) U.S. Cl.
CPC ......... *G02B 13/005* (2013.01); *G02B 23/243* (2013.01)

(56) References Cited

U.S. PATENT DOCUMENTS

| | | | | |
|---|---|---|---|---|
| 3,514,186 | A * | 5/1970 | Poncelet | G02B 13/00 359/792 |
| 4,858,002 | A * | 8/1989 | Zobel | G02B 23/243 348/335 |
| 5,323,268 | A * | 6/1994 | Kikuchi | G02B 6/29311 359/664 |
| 6,134,056 | A * | 10/2000 | Nakamuka | G02B 23/243 600/101 |
| 6,950,242 | B2 * | 9/2005 | Sayag | G02B 13/005 348/340 |
| 8,182,159 | B2 * | 5/2012 | Tanaka | G02B 7/027 385/74 |
| 11,931,004 | B2 * | 3/2024 | Miki | G02B 13/004 |
| 2004/0263994 | A1 * | 12/2004 | Sayag | G02B 13/24 359/664 |
| 2006/0241481 | A1 * | 10/2006 | Itoi | A61B 8/12 600/466 |
| 2006/0268424 | A1 * | 11/2006 | Miyano | G02B 23/243 359/661 |
| 2009/0269009 | A1 * | 10/2009 | Tanaka | G02B 7/027 385/39 |
| 2020/0297203 | A1 * | 9/2020 | Togino | A61B 1/0607 |
| 2021/0145253 | A1 * | 5/2021 | Miki | A61B 1/00195 |

FOREIGN PATENT DOCUMENTS

| | | |
|---|---|---|
| JP | 2017086550 A * | 5/2017 |
| JP | 2018068834 A | 5/2018 |
| WO | 2014091792 A1 | 6/2014 |
| WO | 2017110238 A1 | 6/2017 |
| WO | 2020008613 A1 | 1/2020 |

\* cited by examiner

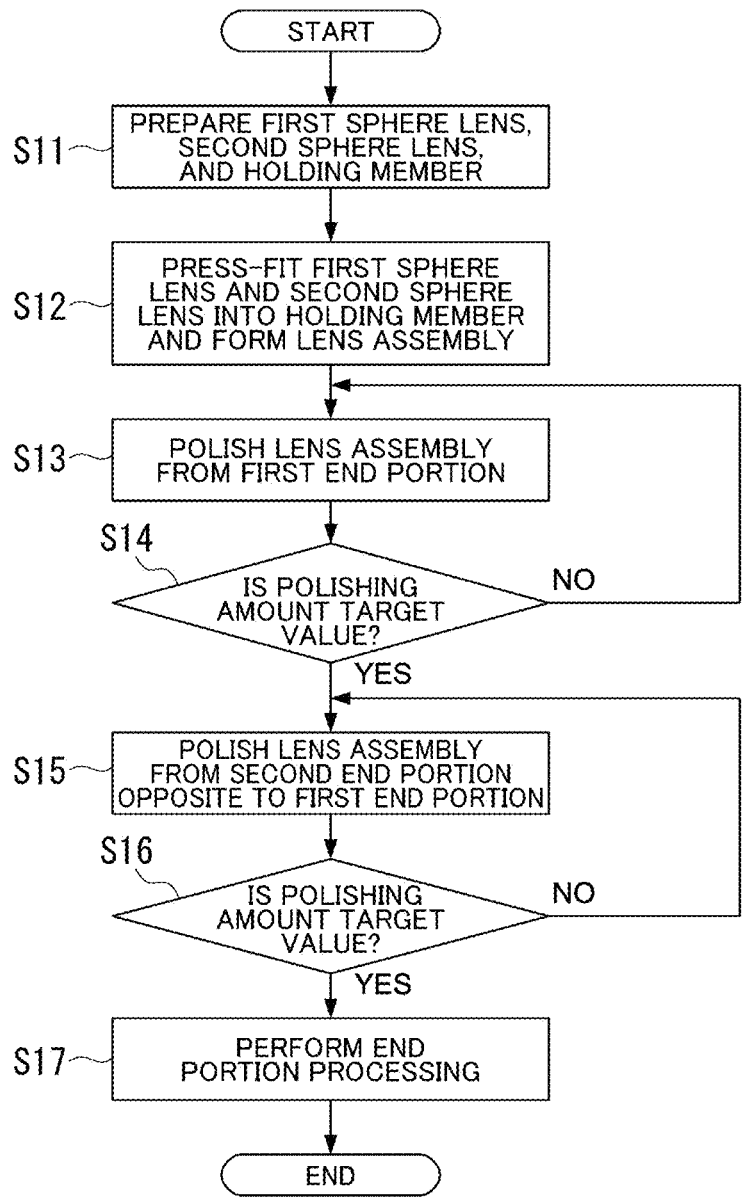

OPTICAL UNIT, FIBER SCANNING DEVICE, AND METHOD FOR MANUFACTURING OPTICAL UNIT

This application is a continuation application of PCT International Application No. PCT/JP2020/024216, filed on Jun. 19, 2020. The content of the PCT International Application is incorporated herein by reference.

TECHNICAL FIELD

The present invention relates to an optical unit, a fiber scanning device, and a method for manufacturing an optical unit.

BACKGROUND ART

An objective optical system is provided at a distal end portion of an endoscope. The objective optical system of the endoscope is used, for example, as an imaging optical system that images a subject or an illumination optical system that illuminates the subject.

For example, PCT International Publication No. WO2017/110238 discloses an objective optical unit in which two plano-convex lenses are arranged such that convex surfaces thereof face each other.

For example, PCT International Publication No. WO2020/008613 discloses an objective optical system in which a lens group in which a solid or liquid optical medium is in close contact with the surface of a sphere lens is arranged such that individual sphere lenses face each other.

Since the objective optical unit described in PCT International Publication No. WO2017/110238 uses the plano-convex lenses, processing becomes more difficult as the outer diameter of each lens is reduced. For example, it becomes difficult to suppress the eccentricity of each convex surface. For this reason, there is a possibility that the optical performance may deteriorate.

Moreover, even when the diameter of each plano-convex lens can be reduced, if the diameter is small, it becomes difficult to distinguish between the convex surface and a flat surface, and it becomes difficult to accurately fix the lens to a lens holder. For this reason, there is a possibility that manufacturing costs may increase.

In the imaging optical system of the endoscope, it is necessary to form an image of an infinite object on an imaging element. However, since the objective optical system described in PCT International Publication No. WO2020/008613 uses a lens in which an optical medium is further added to a thick sphere lens, in order to form an image surface outside the lens group on the image side, it is necessary to form a first surface of the lens group on the object side as a concave surface (refer to FIG. 8 of PCT International Publication No. WO2020/008613). It is more difficult to manufacture a small-diameter biconcave lens than a small-diameter plano-convex lens. Moreover, even when the small-diameter biconcave lens can be manufactured, there is a possibility that assembly becomes difficult.

In a case where the biconcave lens is not used, it is necessary to provide a relay optical system between the lens and the imaging element. Thus, the parts cost increases.

The present disclosure has been made in view of the above problems, and an object thereof is to provide an optical unit and a method for manufacturing the same capable of obtaining excellent optical performance even with a small diameter.

Another object of the present disclosure is to provide a fiber scanning device capable of reducing the diameter by providing the above optical unit.

SUMMARY OF INVENTION

According to an aspect of the present disclosure, an optical unit according to a first aspect includes a first lens configured to be formed in a spherical segment having a first flat surface and a first convex spherical surface; a second lens configured to be formed in a spherical segment having a second flat surface and a second convex spherical surface; and a holding member configured to have a first end portion that surrounds the first lens and a second end portion that surrounds the second lens. The holding member holds the first lens and the second lens with a frictional force such that the first convex spherical surface and the second convex spherical surface are adjacent to each other between the first end portion and the second end portion. The first end portion is located on the same surface as the first flat surface or closer to the second lens than the first flat surface. The second end portion is located on the same surface as the second flat surface or closer to the first lens than the second flat surface.

A fiber scanning device according to a second aspect includes the optical unit according to the first aspect.

A method for manufacturing an optical unit according to a third aspect includes a step of preparing a first sphere lens, a second sphere lens, and a holding member that allows the first sphere lens and the second sphere lens to be press-fitted thereinto, and pressing the first sphere lens and the second sphere lens into an inside of the holding member to form a lens assembly; a first polishing step of surface-polishing the lens assembly from the first end portion into which the first sphere lens is press-fitted to form the first sphere lens in a spherical segment shape; and a second polishing step of surface-polishing the lens assembly from the second end portion into which the second sphere lens is press-fitted to form the second sphere lens in a spherical segment shape.

According to the above first and third aspects, it is possible to provide the optical unit and the method for manufacturing the same that can obtain excellent optical performance even with a small diameter.

According to the second aspect, it is possible to provide the fiber scanning device capable of reducing the diameter by including the optical unit.

BRIEF DESCRIPTION OF DRAWINGS

FIG. 16 is a flowchart showing an example of a method for manufacturing an optical unit according to a modification example of the fourth embodiment of the present disclosure.

DESCRIPTION OF EMBODIMENTS

Figure 1:
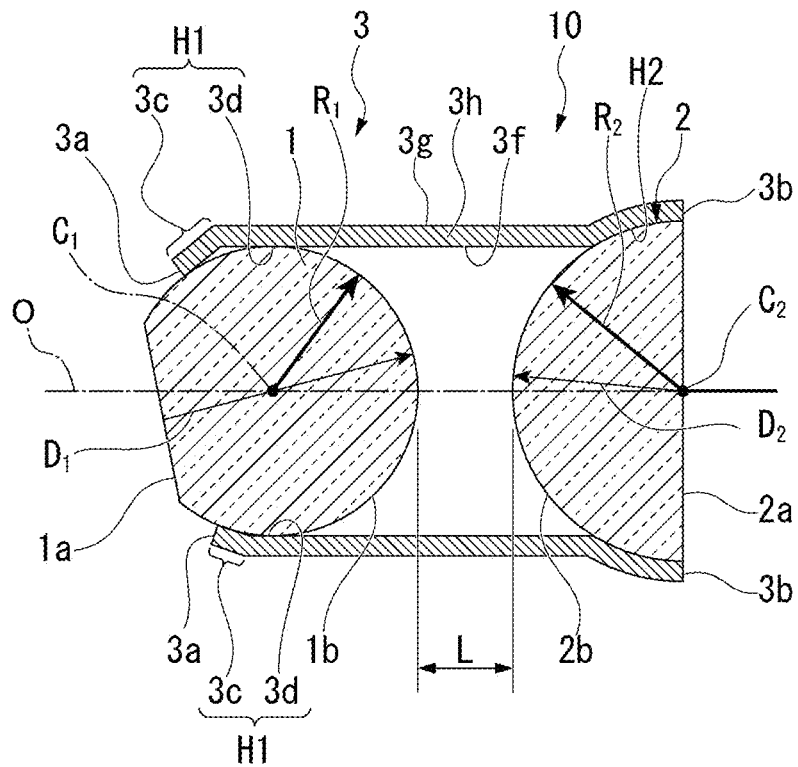
FIG. 1 is a schematic sectional view showing an example of an optical unit according to a first embodiment of the present disclosure.

Hereinafter, embodiments of the present disclosure will be described with reference to the attached drawings. In all the drawings, even in a case where the embodiments are different from each other, the same or equivalent members will be designated by the same reference numerals, and common descriptions will be omitted.

First Embodiment

An optical unit according to a first embodiment of the present disclosure will be described.

FIG. 1 is a schematic sectional view showing an example of the optical unit according to the first embodiment of the present disclosure.

As shown in FIG. 1, an optical unit 10 of the present embodiment can be used as an objective optical system for various equipment. For example, the optical unit 10 may be used for part or all of an imaging optical system that images an object and an illumination optical system that illuminates the object. The type of equipment including the optical unit 10 is not particularly limited. For example, the optical unit 10 may be used in endoscopes, small-sized scanners, small-sized cameras, and the like. The endoscopes may be medical endoscopes or industrial endoscopes. The optical unit 10 can also be used for scanning endoscopes.

The optical unit 10 includes a first lens 1, a second lens 2, and a holding member 3.

In the optical unit 10, the first lens 1 and the second lens 2 are arranged in this order from an object side to an image side.

The first lens 1 is formed in a spherical segment having a first flat surface 1a and a first convex spherical surface 1b.

The spherical segment means a three-dimensional shape formed by cutting a sphere along one plane. The surface of the spherical segment consists of a spherical cap, which is a partially spherical surface, and one circular flat surface at the cut end. The height of the spherical segment means the distance from an intersection point between a normal line passing through the center of the plane and the spherical cap to the plane. The height of the spherical segment may be larger than the radius of the spherical cap or may be equal to or less than the radius of the spherical cap.

The fact that the first lens 1 is formed to have the spherical segment means that the external shape of the first lens 1 is a substantially spherical segment. The shape of the first lens 1 may be a strict spherical segment or may be a shape close to a spherical segment.

For example, the first convex spherical surface 1b is a spherical surface corresponding to the spherical cap, and the first flat surface 1a is a flat surface corresponding to a circular flat surface in the spherical segment. However, the first convex spherical surface 1b and the first flat surface 1a may have an error from the strict spherical surface and the flat surface as long as the optical performance required as the optical unit 10 is satisfied.

For example, as allowable errors, errors caused by manufacturing errors are exemplified. In particular, the first convex spherical surface 1b and the first flat surface 1a may have a larger error than an effective lens region except for the effective lens region through which the beam is transmitted.

For example, allowable errors include wear, chipping, deformation, and the like outside the effective lens region that may occur during a manufacturing process, which will be described below.

However, in the first lens 1, unlike a general plano-convex lens, a columnar portion forming a side surface of the lens is not formed between the first flat surface 1a and the first convex spherical surface 1b.

The fact that the first lens 1 is formed as the spherical segment includes having no columnar portion that forms the side surface of the lens.

The above description also applies to the shape of the second lens 2, which will be described below.

Hereinafter, unless otherwise specified, the spherical surface includes the case of a strictly spherical surface and the case of a surface shape close to the strictly spherical surface. Similarly, the flat surface includes the case of a strictly flat surface and the case of a surface shape close to the strictly flat surface.

The first lens 1 is formed as a spherical segment in which the height of the spherical segment is $D_1$ and the radius of the spherical cap is $R_1$. $D_1$ is not particularly limited as long as $D_1$ is larger than 0 and less than twice $R_1$. As shown in FIG. 1, it is more preferable that $D_1$ is larger than $R_1$ and less than twice $R_1$.

The material of the first lens 1 may be glass or synthetic resin as long as the material has the refractive index and transmittance required as the first lens 1. It is more preferable that the material of the first lens 1 is glass because the material is not easily deformed and an excellent surface accuracy can be obtained. As the glass material, an appropriate glass material for lenses can be used. For example, as the materials of the first lens 1, soda-lime glass, sapphire, and the like, are exemplary examples.

The first flat surface 1a is a smooth surface formed at an end portion of the first lens 1. The first flat surface 1a is formed by polishing processing, for example.

In the example shown in FIG. 1, the first flat surface 1a has a circular external shape with a diameter less than twice $R_1$.

The first convex spherical surface 1b is a portion of the spherical cap of the first lens 1 and is a spherical surface with a radius $R_1$. In the example shown in FIG. 1, the first convex spherical surface 1b extends over a wider region than the effective lens region facing the first convex spherical surface 1b and also constitutes a non-columnar side surface of the first lens 1.

The lens diameter of the first lens 1 is equal to twice the radius $R_1$ of the first convex spherical surface 1b.

The second lens 2 is formed as a spherical segment in which the height of the spherical segment is $D_2$ and the radius of the spherical cap is $R_2$. $D_2$ is not particularly limited as long as $D_2$ is larger than 0 and less than twice $R_2$. Although it is more preferable that $D_2$ is larger than $R_2$ and less than twice $R_2$, as shown in FIG. 1, $D_2$ may be equal to or less than $R_2$.

The material of the second lens 2 may be glass or synthetic resin as long as the material has the refractive index and transmittance required as the second lens 2. It is more preferable that the material of the second lens 2 is glass.

The refractive index of the second lens 2 may be the same as or different from that of the first lens 1. The material of the second lens 2 can be selected from materials suitable for the first lens 1.

The second flat surface 2a is a smooth surface formed at an end portion of the second lens 2. The second flat surface 2a is formed by polishing processing, for example.

In the example shown in FIG. 1, the second flat surface 2a has a circular external shape with a diameter equal to or less than twice $R_2$.

The second convex spherical surface 2b is a portion of the spherical cap of the second lens 2 and is a spherical surface with a radius $R_2$. In the example shown in FIG. 1, the second convex spherical surface 2b extends over a wider region than the effective lens region facing the first convex spherical surface 1b and also constitutes a non-columnar side surface of the second lens 2.

The radius $R_2$ of the second convex spherical surface 2b may be the same as or different from the radius $R_1$ of the first convex spherical surface 1b. In the example shown in FIG. 1, $R_2$ is larger than $R_1$.

The lens diameter of the second lens 2 is equal to the outer diameter of the second convex spherical surface 2b.

A holding member 3 holds the first lens 1 and the second lens 2. Although the shape of the holding member 3 is not particularly limited as long as the holding member can hold the first lens 1 and the second lens 2, at least a first end portion 3a and a second end portion 3b are formed at both ends in the axial direction.

For example, the holding member 3 may be a tubular shape having a circular section, a tubular shape having a polygonal section, a housing elongated in one direction, or the like. The holding member 3 may or may not have an opening on the side surface.

The first end portion 3a forms an opening portion that surrounds the side surface of the first lens 1. The first end portion 3a may be formed in an annular shape that is continuous in a circumferential direction, or may be formed in a plurality of spots spaced apart in the circumferential direction.

A first holding portion H1 that holds the first lens 1 is formed in the vicinity of the first end portion 3a. The first holding portion H1 may hold the side surface of the first lens 1 over the entire circumference, or may hold the side surface of the first lens 1 at a plurality of spots spaced apart in the circumferential direction.

The shape of the first holding portion H1 is not particularly limited as long as the first holding portion has a shape that can hold the first lens 1 in contact with the first lens 1. For example, the first holding portion H1 may be formed as a recessed portion that is recessed outward from an inner peripheral surface 3f, or may be formed as a protruding portion that protrudes inward from the inner peripheral surface 3f. The first holding portion H1 may have a curved surface or a flat surface that abuts against the side surface of the first lens 1. The contact state between the first holding portion H1 and the first lens 1 may be any of the point contact, line contact, and surface contact.

The second end portion 3b is an end portion of the holding member 3 opposite to the first end portion 3a in the axial direction. The second end portion 3b forms an opening portion that surrounds the side surface of the second lens 2. Similar to the first end portion 3a, the second end portion 3b may be formed in an annular shape that is continuous in the circumferential direction, or may be formed at a plurality of spots spaced apart in the circumferential direction.

The second holding portion H2 that holds the second lens 2 is formed in the vicinity of the second convex spherical surface 2b or the second end portion 3b. The second holding portion H2 may hold the side surface of the second lens 2 over the entire circumference, or may hold the side surface of the second lens 2 at a plurality of spots spaced apart in the circumferential direction.

The shape of the second holding portion H2 is not particularly limited as long as the second holding portion has a shape that can hold the second lens 2. The shape of the second holding portion H2 can be the same shape as the example of the above-described shape of the first holding portion H1. The second holding portion H2 and the second lens 2 can come into contact with each other in the same state as the above-described contact state between the first holding portion H1 and the first lens 1.

The material of the holding member 3 may be metal or synthetic resin. It is more preferable that the holding member 3 is made of metal from the viewpoint that stable holding performance can be easily obtained because the holding member 3 does not easily expand even when a temperature change occurs. As examples of the material of the holding member 3, stainless steel and aluminum alloy are exemplary examples.

In the example shown in FIG. 1, the holding member 3 has a tubular shape with a circular section. Hereinafter, unless otherwise specified, the example shown in FIG. 1 will be described.

The portion of the holding member 3 excluding the first holding portion H1 and the second holding portion H2 at both end portions is a cylindrical portion 3h having the inner peripheral surface 3f and the outer peripheral surface 3g. The diameter of the inner peripheral surface 3f is slightly smaller than the outer diameter of the first lens 1. For this reason, it is possible to press-fit and fix the first lens 1 and the second lens 2 inside the inner peripheral surface 3f.

The first holding portion H1 consists of an annular portion 3d and a diameter-reduced portion 3c.

The annular portion 3d is formed at an end portion of the cylindrical portion 3h near the first end portion 3a. The annular portion 3d is in close contact with the side surface of the first lens 1. The annular portion 3d tightens and holds the side surface of the first lens 1 from the outer peripheral side. For this reason, no adhesive or the like is interposed between the annular portion 3d and the first lens 1. The first lens 1 is held by the annular portion 3d with a frictional force.

Since the annular portion 3d extends along the outer diameter of the first lens 1, the annular portion bulges slightly more than the cylindrical portion 3h.

The annular portion 3d is formed by press-fitting the first lens 1 into the cylindrical portion 3h. For this reason, a same cylindrical portion similar to the cylindrical portion 3h surrounds the first lens 1 between the annular portion 3d and the diameter-reduced portion 3c while being separated from the first lens 1.

The diameter-reduced portion 3c is a tubular portion of which the diameter is reduced in a tapered shape from the end portion of the annular portion 3d near the first end portion 3a toward the first end portion 3a. An inner surface of the diameter-reduced portion 3c abuts against the first convex spherical surface 1b of the first lens 1.

For this reason, the first end portion 3a is located closer to the second lens 2 than the first flat surface 1a.

Since the inner diameter of a distal end portion of the diameter-reduced portion 3c is further smaller than that of the cylindrical portion 3h, the diameter-reduced portion 3c includes a function of holding the first lens 1 and a function of retaining the first lens 1 in the axial direction facing outward from the first end portion 3a.

However, the diameter-reduced portion 3c may not abut against the first lens 1 in a case where a required holding force can be obtained only by the annular portion 3d. In this case, the diameter-reduced portion 3c is not included in the first holding portion H1 and has only the retaining function.

The second holding portion H2 is formed between the end portion of the cylindrical portion 3h near the second end portion 3b, and the second end portion 3b. The second holding portion H2 is a recessed portion that is in close contact with the second convex spherical surface 2b of the second lens 2.

The second holding portion H2 tightens and holds the second convex spherical surface 2b, which forms the side surface of the second lens 2, from the outer peripheral side. For this reason, no adhesive or the like is interposed between the second holding portion H2 and the second lens 2. The second lens 2 is held by the second holding portion H2 with a frictional force.

Since the second holding portion H2 extends along the outer diameter of the second lens 2, the second holding portion bulges outward from the cylindrical portion 3h.

The second holding portion H2 is formed by press-fitting the first lens 1 into the cylindrical portion 3h.

The second end portion 3b is formed at the end portion of the second holding portion H2 opposite to the cylindrical portion 3h.

The second end portion 3b may be located closer to the first lens 1 than the second flat surface 2a, but in the example shown in FIG. 1, the second end portion 3b is located on the same surface as the second flat surface 2a.

As described above, the holding member 3 of the optical unit 10 holds the first lens 1 and the second lens 2 such that the first convex spherical surface 1b and the second convex spherical surface 2b are adjacent to each other between the first end portion 3a and the second end portion 3b.

An axis O connecting a sphere center $C_1$ of the first convex spherical surface 1b and a sphere center $C_2$ of the second convex spherical surface 2b is coaxial with a central axis of the cylindrical portion 3h.

The first flat surface 1a, the first convex spherical surface 1b, the second convex spherical surface 2b, and the second flat surface 2a are arranged in this order on the axis O.

In the example shown in FIG. 1, the first flat surface 1a is inclined non-perpendicularly to the axis O, and the second flat surface 2a is orthogonal to the axis O. However, the respective inclination angles between the first flat surface 1a and the second flat surface 2a and the axis O are not particularly limited as long as required beams can be incident and emitted.

However, it is more preferable that a flat surface formed on an image side is orthogonal to the axis O in that an image surface easily formed outside the flat surface.

The first lens 1 and the second lens 2 held in this way constitute the same optical system as an optical system consisting of two plano-convex lenses of which the convex surfaces face each other. Although either of the first lens 1 and the second lens 2 may be arranged on an object side, hereinafter, a description will be given assuming that the first lens 1 is arranged on the object side and the second lens 2 is arranged on the image side. The axis O is assumed to be an optical axis of the optical system. For this reason, there is a case where the axis O may be described as the optical axis O.

A surface spacing between the first flat surface 1a and the first convex spherical surface 1b is about $D_1$, a surface spacing (air spacing) between the first convex spherical surface 1b and the second convex spherical surface 2b is L, and a surface spacing between the second convex spherical surface 2b and the second flat surface 2a is $D_2$.

L may be any appropriate value equal to or larger than 0. However, L may satisfy the following Formula (1). In this case, the field of view, that is, the angle of view of the optical system can be increased.

[Formula 1]

$$L \leq (R_1 + R_2)\left(\frac{n_2}{\sqrt{n_2^2 - 1}} - 1\right) \quad (1)$$

Figure 2:
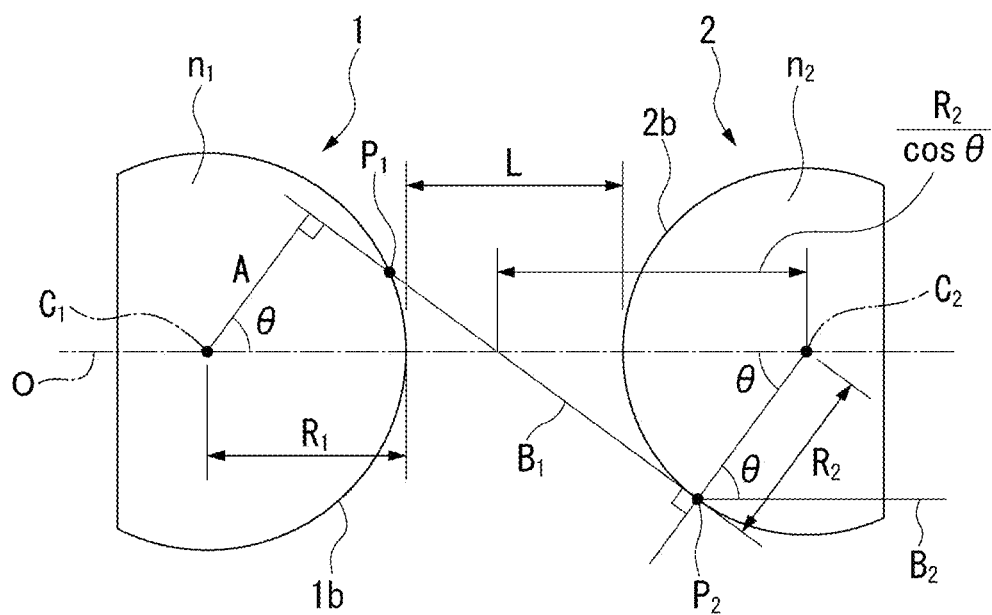
FIG. 2 is a schematic diagram illustrating a method of deriving Formula (1).

Here, as described above, L, $R_1$, and $R_2$ are the surface spacing between the first convex spherical surface 1b and the second convex spherical surface 2b, the radius of the first convex spherical surface 1b, and the radius of the second convex spherical surface 2b, respectively. $n_2$ is the refractive index of the second lens 2. In FIG. 2, $n_1$ is the refractive index of the first lens 1.

A method of deriving Formula (1) will be briefly described.

FIG. 2 is a schematic diagram illustrating the method of deriving Formula (1).

In the optical system of the optical unit 10, the condition is derived that a light ray with the largest image height among the light rays parallel to the optical axis O on the image side passes through the optical system without being vignetted. When this condition is satisfied, all the light rays within the effective diameter of the first lens 1 form an image, and the maximum field of view, that is, the maximum angle of view can be secured.

As shown in FIG. 2, it is assumed that a light ray $B_1$ incident from a point $P_1$ on the first convex spherical surface 1b to a point $P_2$ on the second convex spherical surface 2b is refracted by the second convex spherical surface 2b like a light ray $B_2$, and travels parallel to the optical axis O. In this case, a distance A from a sphere center $C_1$ of the first convex spherical surface 1b to the light ray $B_1$ is represented by the following Formula (a).

[Formula 2]

$$A = \cos\theta\left\{(R_1 + L) - \left(\frac{R_2}{\cos\theta} - R_2\right)\right\} \quad (a)$$

Here, θ is an acute angle among the angles formed between a line segment $C_1P_2$ and the light ray $B_2$.

The condition under which the light ray $B_1$ can be emitted from the first convex spherical surface 1b is that A is equal to or less than $R_1$. The following Formula (b) is obtained by substituting Formula (a) in $A \leq R_1$.

[Formula 3]

$$L \leq (R_1 + R_2)\left(\frac{1}{\cos\theta} - 1\right) \quad (b)$$

Since the condition under which refraction occurs at the point $P_2$ is a condition that the incident angle is 90° and the emitting angle is θ, the following Formula (c) is established according to the Snell's law. In Formula (c), 1 is the refractive index of air.

The following Formula (c) can be rewritten as the following Formula (d). Formula (1) is obtained by substituting the following Formula (d) in Formula (b).

[Formula 4]

$$1 \times \sin 90° = n_2 \sin\theta \quad (c)$$

$$\theta = \frac{\sqrt{n_2^2 - 1}}{n_2} \quad (d)$$

In the optical unit 10, it is more preferable that the lens diameter of the first lens 1, the lens diameter of the second lens 2, and the inner diameter of the cylindrical portion 3h of the holding member 3 have sizes such that the deformation of the cylindrical portion 3h is not excessively large in a case where the first lens 1 and the second lens 2 are press-fitted into the cylindrical portion 3h. In this case, the degree of coaxiality between the first lens 1 and the second lens 2 is improved because the amount of deformation of the cylindrical portion 3h is reduced.

Specifically, the optical unit 10 may satisfy the following Formula (2).

[Formula 5]

$$0.8 d_b < d_c \leq d_a \quad (2)$$

Here, $d_a$ is the smaller one of the diameter of the first lens 1 and the diameter of the second lens 2, and $d_b$ is the larger one. $d_c$ is the inner diameter of the cylindrical portion 3h, that is, the inner diameter of the holding member 3 between the first lens 1 and the second lens 2.

In the example shown in FIG. 1, $d_a$ is twice $R_1$ and $d_b$ is twice $R_2$.

When $d_c$ is equal to or less than $0.8 \times d_b$, the deformation of the holding member 3 during the press-fitting becomes excessively large. Thus, a larger-diameter lens tends to be eccentric with respect to the optical axis O.

When $d_c$ is larger than $d_a$, the holding force of a smaller-diameter lens will not be obtained.

In a case where $d_c$ and $d_a$ are equal to each other, a lens is held with the frictional force of a contact portion between the smaller-diameter lens and the holding member 3, although the lens is not press-fitted. In particular, in a case where there is a manufacturing error between the lens and the holding member 3, even when the average diameters are equal to each other, the holding force is generated because the lens and the holding member are fitted to each other in a partially press-fitted state.

It is more preferable that the optical system of the optical unit 10 can form an image of an infinite object outside the second lens 2. Considering that an imaging element may be arranged in close contact with the second flat surface 2a, the outside of the second lens 2 includes on the second flat surface 2a and the outside of the second flat surface 2a.

For example, the optical system of the optical unit 10 may satisfy the following Formula (3). The meaning of each reference numeral in the following Formula (3) is the same as the above-described one.

[Formula 6]

$$D_2 \leq \frac{n_2\{R_2L(1-n_1) + R_1R_2\}}{R_1(n_2-1) + L(n_2-1)(1-n_1) + R_2(n_1-1)} \quad (3)$$

A method of deriving Formula (3) will be briefly described.

Figure 3:
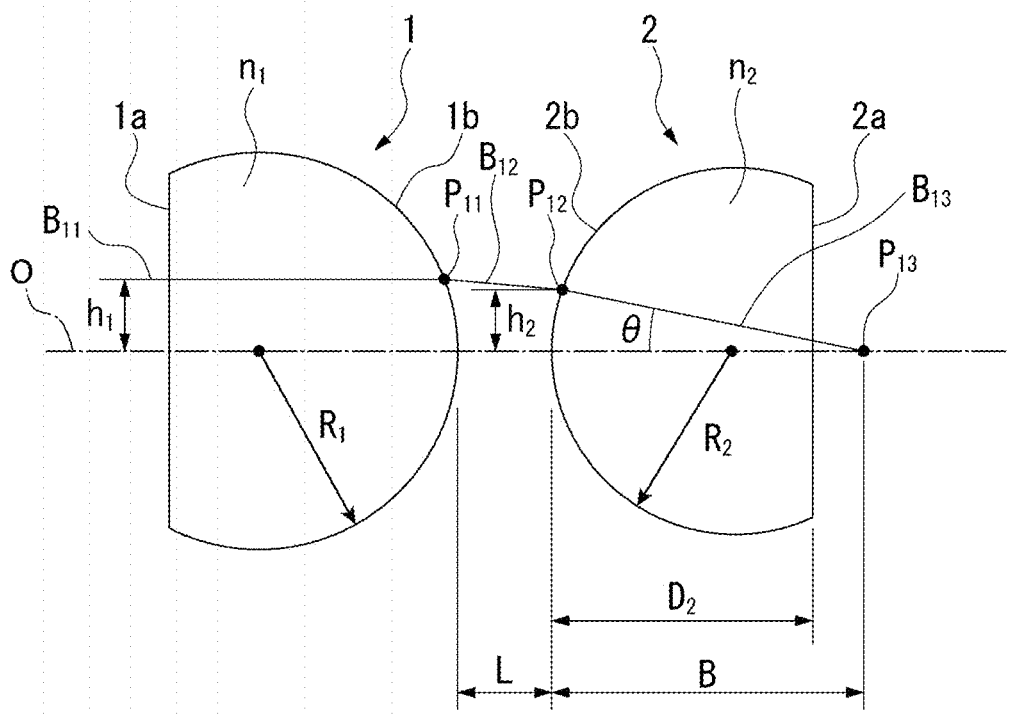
FIG. 3 is a schematic diagram illustrating a method of deriving Formula (3).

FIG. 3 is a schematic diagram illustrating the method of deriving Formula (3).

Formula (3) is derived from paraxial ray tracing in the optical system of optical unit 10 as follows.

As shown in FIG. 3, a light ray $B_{11}$ parallel to the optical axis O and incident on the first flat surface 1a at an image height $h_1$ is refracted at a point $P_{11}$ on the first convex spherical surface 1b and is incident on a point $P_{12}$ on the second convex spherical surface 2b as a light ray $B_{12}$. The image height of the point $P_{12}$ is $h_2$ (here, $h_2 < h_1$). The light ray $B_{12}$ is refracted by the second convex spherical surface 2b and reaches a point $P_{13}$ on the optical axis O as a light ray $B_{13}$.

Assuming that the acute angle of the angles between the optical axis O and the light ray $B_{13}$ is θ, the following Formula (e) is established from matrix ray tracing in which a paraxis is assumed.

[Formula 7]

$$\begin{pmatrix} n_2\theta \\ h_2 \end{pmatrix} = \begin{pmatrix} 1 & \frac{n_2-1}{R_2} \\ 0 & 1 \end{pmatrix} \begin{pmatrix} 1 & 0 \\ -L & 1 \end{pmatrix} \begin{pmatrix} 1 & \frac{1-n_1}{R_1} \\ 0 & 1 \end{pmatrix} \quad (e)$$

A distance B on the optical axis O between the first convex spherical surface 1b and the point $P_{13}$ is represented by the following Formula (f), assuming the paraxis.

[Formula 8]

$$B = h_2/\theta \quad (f)$$

By substituting $h_2$ and θ obtained from Formula (e) in Formula (f), B is represented like a right side of Formula (3). That is, Formula (3) represents the condition that $D_2$ is equal to or less than B.

An example of a method for manufacturing the optical unit 10 of the present embodiment will be briefly described.

A first sphere lens consisting of a ball with a diameter $R_1$, a second sphere lens consisting of a ball with a diameter $R_2$, and a cylindrical member having a shape in which the cylindrical portion 3h is extended longer than the holding member 3 are prepared.

After that, the first sphere lens and the second sphere lens are press-fitted into both end portions of the cylindrical member to form a lens assembly. In this case, the first sphere lens is press-fitted so as to protrude to be larger than $(2 \times R_1 - D_1)$ from an end surface of the cylindrical member.

The second sphere lens is press-fitted inside the cylindrical member such that an inter-surface distance between the second sphere lens and the first sphere lens is L. The length of the cylindrical member is set to a length such that when the second sphere lens is press-fitted, the second sphere lens does not stick out of the cylindrical member, or even when the second sphere lens sticks out, the second sphere lens sticks out only by less than $(2 \times R_2 - D_2)$ from the end surface of the cylindrical member.

When the first sphere lens and the second sphere lens are press-fitted, the end portion of the cylindrical member is deformed along the side surfaces of the first sphere lens and the second sphere lens.

After that, both end portions of the lens assembly are surface-polished to form the first flat surface 1a and the second flat surface 2a. Accordingly, each of the first sphere lens and the second sphere lens is formed as each of the first lens 1 and the second lens 2 of the spherical segment.

According to the above-described positional relationship between the press-fitting positions of the first and second sphere lenses and the end surface of the cylindrical member, an end portion of the cylindrical member on a side where the first sphere lens is press-fitted is not polished until the first flat surface 1a is formed.

An end portion of the cylindrical member on a side where the second sphere lens is press-fitted is surface-polished together with the second sphere lens. As a result, the second end portion 3b is formed on the same surface as the second flat surface 2a.

After that, the end portion of the cylindrical member into which the first sphere lens is press-fitted is compressed toward the first lens 1 to form the diameter-reduced portion 3c.

The optical unit 10 as shown in FIG. 1 is manufactured as described above.

According to the optical unit 10 of the present embodiment, the first sphere lens and the second sphere lens are held by the cylindrical member by press-fitting the first sphere lens and the second sphere lens into the cylindrical member. Since the sphere lens does not have a specific optical axis, it is unnecessary to align the central axis of the cylindrical member with the optical axis.

Moreover, by press-fitting the first sphere lens and the second sphere lens into the cylindrical member, the sphere center of each of the first sphere lens and the second sphere lens is aligned with the central axis of the cylindrical member.

Since the positional relationship between the first sphere lens and the second sphere lens is fixed with respect to the cylindrical member with the holding force resulting from the press-fitting, there is no concern that the mutual positional relationship will deviate during the surface-polishing.

For this reason, compared to a case where the first lens 1 and the second lens 2 of the spherical segment are manufactured in advance and then arranged on the holding member 3, the disposition accuracy of the first lens 1 and the second lens 2 with respect to the holding member 3 can be improved.

According to the optical unit 10, an optical system similar to two plano-convex lenses is formed, but the first lens 1 and the second lens 2 are held by the holding member 3. Therefore, for example, a step of machining a columnar side surface can be omitted. For this reason, the manufacturing process is simplified compared to a case where two plano-convex lenses are manufactured and held by the holding member 3. Thus, the parts cost and the manufacturing cost can be reduced.

In a case where the two plano-convex lenses are manufactured, there is a concern that the lens surfaces are decentered when the lens side surfaces are formed. However, in the present embodiment, the occurrence of such a manufacturing error can be prevented.

As described above, according to the optical unit 10 and the method for manufacturing the optical unit in the present embodiment, excellent optical performance can be obtained even with a small diameter.

Second Embodiment

An optical unit according to a second embodiment of the present disclosure will be described.

Figure 4:
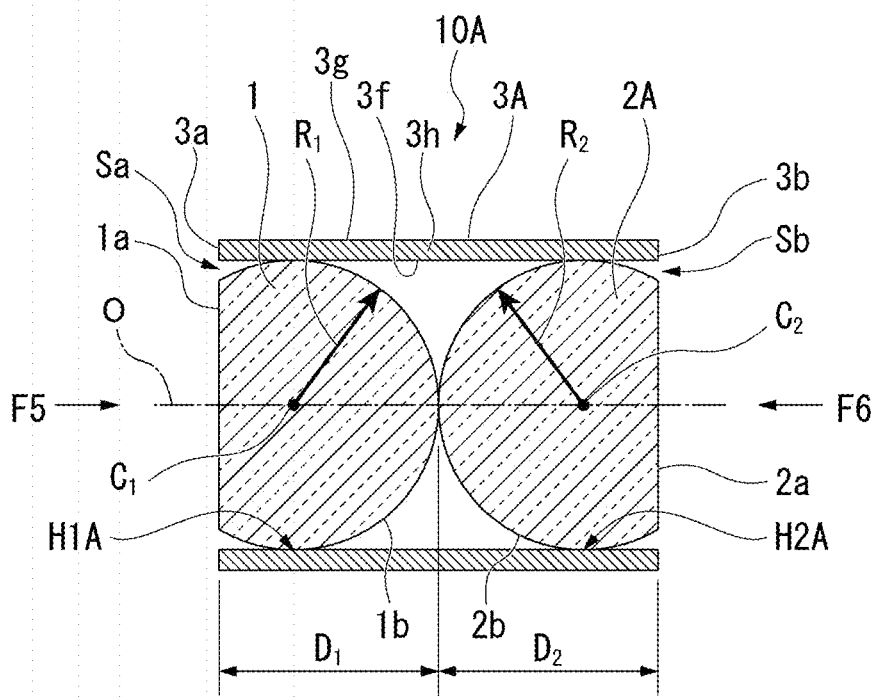
FIG. 4 is a schematic sectional view showing an example of an optical unit according to a second embodiment of the present disclosure.
Figure 5:
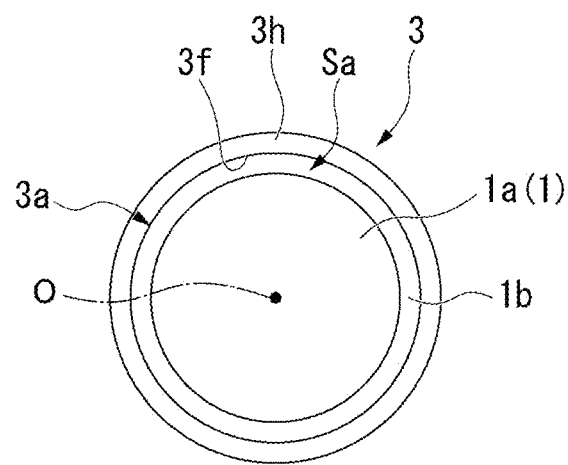
FIG. 5 is a side view of FIG. 4 as viewed from F5.
Figure 6:
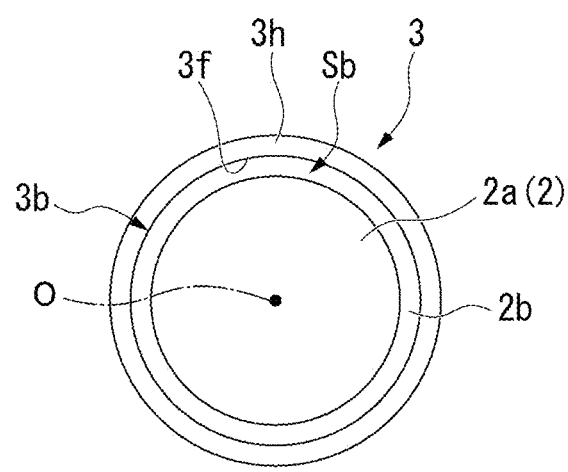
FIG. 6 is a side view of FIG. 4 as viewed from F6.

FIG. 4 is a schematic sectional view showing an example of the optical unit according to the second embodiment of the present disclosure. FIG. 5 is a side view of FIG. 4 as viewed from F5. FIG. 6 is a side view of FIG. 4 as viewed from F6.

As shown in FIG. 4, an optical unit 10A of the present embodiment includes a second lens 2A and a holding member 3A instead of the second lens 2 and holding member 3 of the optical unit 10 of the first embodiment. Hereinafter, differences from the first embodiment will mainly be described.

The first lens 1 in the present embodiment has the first flat surface 1a and the first convex spherical surface 1b, similarly to the example shown in FIG. 1 in the first embodiment. A height $D_1$ of the spherical segment is larger than the radius $R_1$ of the first convex spherical surface 1b and smaller than twice the radius $R_2$ of the first convex spherical surface 1b. However, in the present embodiment, the first flat surface 1a is arranged on the same surface as the first end portion 3a of the holding member 3A, which will be described below.

Similar to the second lens 2, the second lens 2A is a spherical segment having the second flat surface 2a and the second convex spherical surface 2b. However, unlike the spherical segment shown in FIG. 1, a height $D_2$ of the spherical segment is larger than the radius $R_2$ of the second convex spherical surface 2b and smaller than twice the radius $R_2$ of the second convex spherical surface 2b.

Moreover, in the present embodiment, $R_2$ is equal to or close to $R_1$.

The holding member 3A is a cylinder having the first end portion 3a and the second end portion 3b at axial end portions thereof. The material of the holding member 3A is the same as that of the holding member 3.

A first holding portion H1A similar to the annular portion 3d in the first embodiment is formed near the first end portion 3a. A second holding portion H2A similar to the annular portion 3d in the first embodiment is formed near the second end portion 3b.

Each of the first holding portion H1A and the second holding portion H2A is formed by press-fitting each of the first lens 1 and the second lens 2 into the cylindrical portion 3h.

In the holding member 3A, the portion other than the first holding portion H1A and the second holding portion H2A is the cylindrical portion 3h similar to that of the first embodiment.

For this reason, Formula (2) is satisfied in the optical unit 10A.

In the optical unit 10A, the first convex spherical surface 1b and the second convex spherical surface 2b of the first lens 1 and the second lens 2A abut against each other.

The total length of the holding member 3A is $(D_1+D_2)$, and each of the first flat surface 1a and the second flat surface 2a is located on the same surface as each of the first end portion 3a and the second end portion 3b of the second convex spherical surface 2b.

Similar to the first embodiment, the axis O passing through the sphere center $C_1$ of the first convex spherical surface 1b and the sphere center $C_2$ of the second convex spherical surface 2b is coaxial with a central axis of the holding member 3A.

As shown in FIG. 5, the first flat surface 1a as viewed from the first end portion 3a side is located inside the inner peripheral surface 3f away from the cylindrical portion 3h. A first space Sa that spreads in an annular shape as viewed from a direction along the optical axis O is formed between the first convex spherical surface 1b adjacent to the first flat surface 1a and the inner peripheral surface 3f.

As shown in FIG. 6, the second flat surface 2a as viewed from the second end portion 3b side is located inside the inner peripheral surface 3f away from the cylindrical portion 3h. A second space Sb that spreads in an annular shape as viewed from the direction along the optical axis O is formed between the second convex spherical surface 2b adjacent to the second flat surface 2a and the inner peripheral surface 3f.

In the optical unit 10A, the first flat surface 1a, the first convex spherical surface 1b, the second convex spherical surface 2b, and the second flat surface 2a are arranged side by side in this order on the optical axis O from the object side toward the image side. The inter-surface distance L between the first convex spherical surface 1b and the second convex spherical surface 2b is 0, and Formula (1) is satisfied.

Moreover, in the present embodiment, Formula (3) is satisfied.

Such an optical unit 10A can be manufactured in substantially the same manner as in the first embodiment by press-fitting the first sphere lens and the second sphere lens inside a cylindrical member similar to the cylindrical portion 3h to form a lens assembly. However, the manufacturing method of the present embodiment is different in that when the first flat surface 1a is formed, the end portion of the cylindrical member is surface-polished together with the first sphere lens, and the diameter-reduced portion 3c is not formed.

The action of the optical system of the optical unit 10A will be described.

Figure 7:
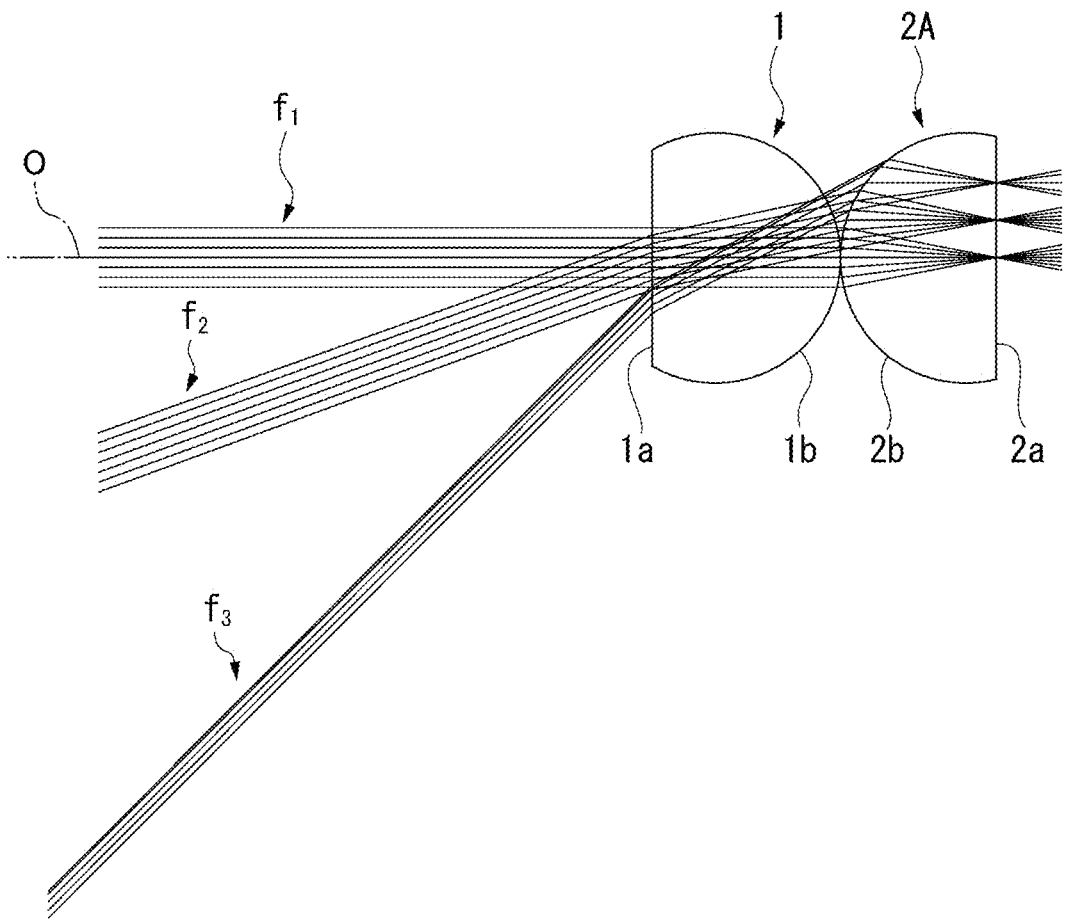
FIG. 7 is a diagram showing an example of optical simulation in the optical unit according to the second embodiment of the present disclosure.

FIG. 7 is a diagram showing an example of optical simulation in the optical unit according to the second embodiment of the present disclosure.

In FIG. 7, light rays when $R_1=R_2=200$ (μm), $D_1=300$ (μm), $D_2=250$ (μm), and $n_1=n_2=1.5$ in the optical unit 10A are drawn. In this case, since the value of B in Formula (f) is 350 μm, Formula (3) is satisfied.

Beams $f_1$, $f_2$, and $f_3$ are parallel beams on the axis, at both angles of view of 40°, and at both angles of view of 90°, respectively. Each beam is drawn such that the numerical aperture (hereinafter referred to as NA) on the image surface is constant. Although not shown, the maximum both angles of view of the present optical system were about 100°. The image surface was located at a working distance (hereinafter referred to as WD) of 25 μm. However, even when $D_2$ is reduced, an imaging position does not change significantly. For example, when $D_2$ was 200 μm, WD was 60 μm.

As an example of such an optical system, an optical system in which the brightness is determined by the optical system on the image side is exemplified. For example, an illumination optical system that performs irradiation with light from an optical fiber arranged on the image surface toward the object side, an observation optical system that performs an observation through a diaphragm provided on the image side, and the like, are exemplified. Specifically, optical systems used in scanning endoscopes, rod lens rigid endoscopes, fiberscopes, and the like, are exemplary examples.

Although not particularly shown, chromatic aberration was also excellent at NA of 0.25.

Examples 1 to 7 of the optical unit 10A were manufactured under the conditions shown in the following Table 1. In Table 1, the lens means the first lens 1 and the second lens 2. However, $D_1$ of the first lens 1 was set to 300 μm, and $D_2$ of the second lens 2 was set to 250 μm. The outer diameter and inner diameter of the holding member represent the outer diameter and inner diameter of the cylindrical portion 3h before the press-fitting.

TABLE 1

| | Lens | | | Holding Member | | | |
|---|---|---|---|---|---|---|---|
| | Glass Material | Refractive Index | Lens Diameter (mm) | Material | Outer Diameter (mm) | Inner diameter (mm) | Image Quality |
| Example 1 | Soda-lime Glass | 1.5 | 0.4 | Stainless Steel | 0.45 | 0.4 | Excellent |
| Example 2 | Soda-lime Glass | 1.5 | 0.5 | Stainless Steel | 0.45 | 0.4 | Excellent |
| Example 3 | Soda-lime Glass | 1.5 | 0.4 | Stainless Steel | 0.5 | 0.39 | Excellent |
| Example 4 | Soda-lime Glass | 1.5 | 0.36 | Stainless Steel | 0.45 | 0.35 | Excellent |
| Example 5 | Soda-lime Glass | 1.5 | 0.3 | Stainless Steel | 0.41 | 0.29 | Excellent |
| Example 6 | Sapphire | 1.75 | 0.4 | Stainless Steel | 0.45 | 0.35 | Excellent |
| Example 7 | Sapphire | 1.75 | 0.4 | Stainless Steel | 0.5 | 0.39 | Excellent |

Image quality evaluation was performed by observing an image of an angle-of-view chart through the optical unit 10A of each example through a microscope objective lens with NA of 0.25. The angle-of-view chart was illuminated with scattered light from the back surface. The distance between the angle-of-view chart and the optical unit 10A was set to 10 mm.

As shown in Table 1, since the images of the observed angle-of-view charts were all clear, the image quality was determined to be excellent.

As described above, according to the optical unit 10A and the method for manufacturing the optical unit in the present embodiment, excellent optical performance can be obtained even with a small diameter.

Third Embodiment

An optical unit according to a third embodiment of the present disclosure will be described.

Figure 8:
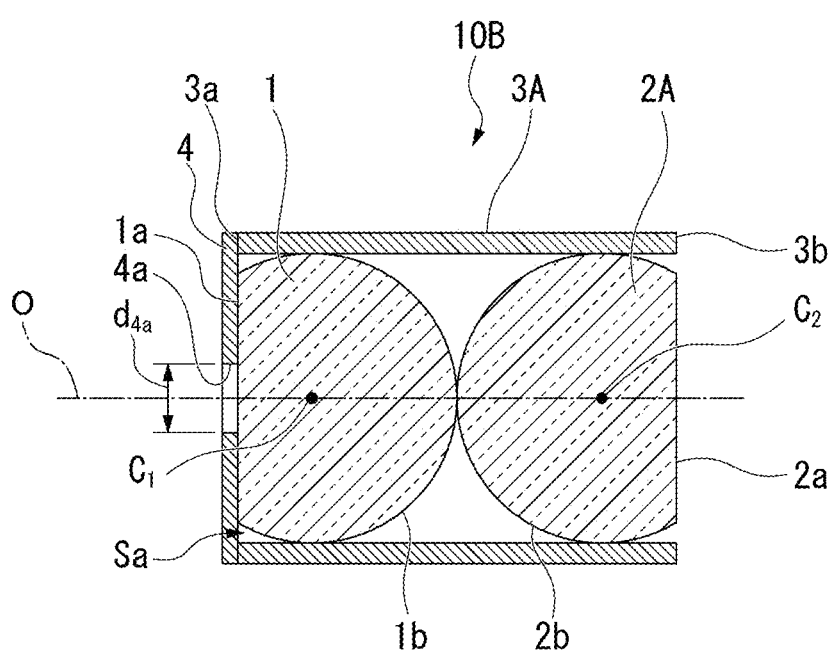
FIG. 8 is a schematic sectional view showing an example of an optical unit according to a third embodiment of the present disclosure.

FIG. 8 is a schematic sectional view showing an example of the optical unit according to the third embodiment of the present disclosure.

As shown in FIG. 8, an optical unit 10B of the present embodiment is configured such that a diaphragm 4 is further added to the first lens 1, the second lens 2A, and the holding member 3A similar to the optical unit 10A of the second embodiment. Hereinafter, differences from the second embodiment will mainly be described.

The diaphragm 4 restricts the beam diameter of a beam incident on the first flat surface 1a.

The configuration of the diaphragm 4 is not particularly limited as long as the diaphragm can restrict the beam diameter of the beam incident on the first flat surface 1a. In an example shown in FIG. 8, the diaphragm 4 is a flat plate through which an opening portion 4a passes. The opening portion 4a is, for example, a circular hole with a diameter $d_{4a}$. The center of the opening portion 4a is located on the optical axis O.

A method for joining the diaphragm 4 is not particularly limited as long as the diaphragm can be fixed to at least one of the holding member 3 and the first lens 1. For example, the diaphragm 4 may be made to adhere using an adhesive.

The adhesion portion may be, for example, one or both of the first end portion 3a and the first flat surface 1a. For example, the diaphragm 4 may be made to adhere with an adhesive applied to the first space Sa. In this case, the adhesive is less likely to stick out to the inside of the opening portion 4a and the outside of the holding member 3A.

As in the example shown in FIG. 8, when the outer diameter of the diaphragm 4 is matched with the outer diameter of the holding member 3A, the alignment between the opening portion 4a and the optical axis O becomes easier.

When the diaphragm 4 is made to adhere to the first end portion 3a and the first flat surface 1a without gaps, a distal end side of the optical unit 10B can be sealed.

The material of the diaphragm 4 is not particularly limited as long as the material is a material having a light shielding property.

The size of the opening portion 4a is determined depending on the optical performance required for the optical unit 10B.

Figure 9:
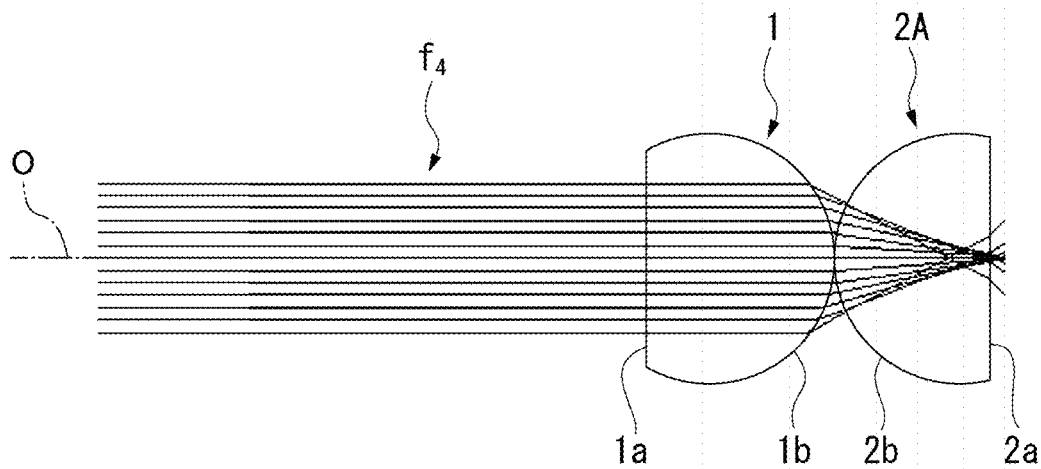
FIG. 9 is a diagram showing an example of optical simulation of an on-axis beam in an optical unit having no diaphragm.
Figure 10:
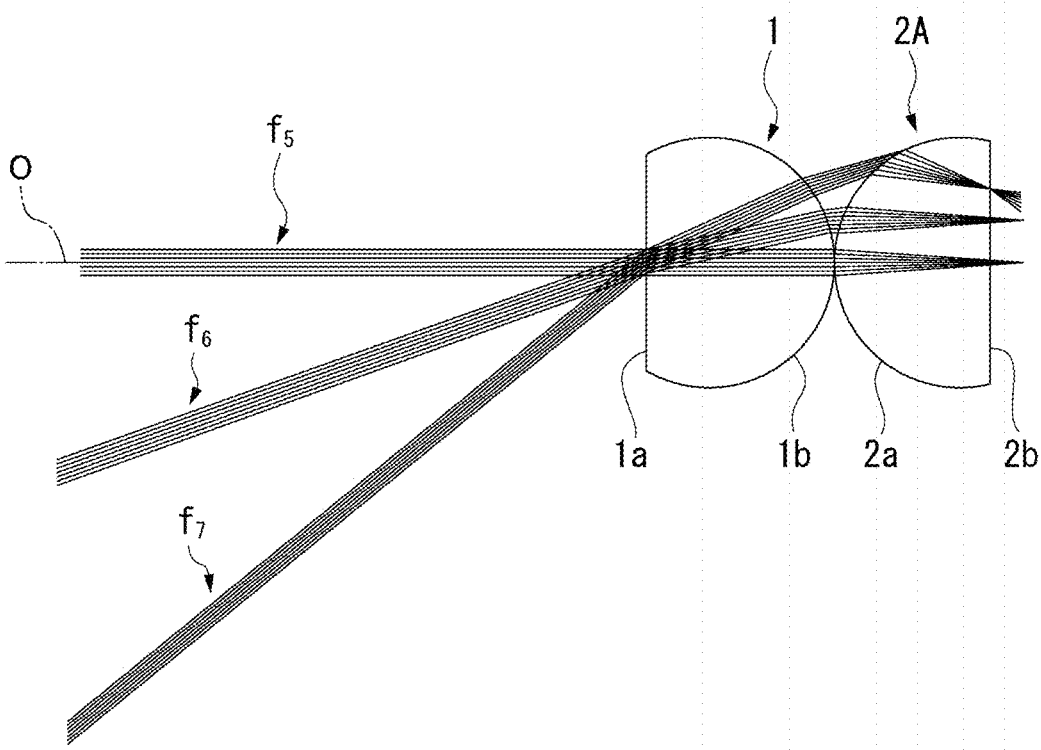
FIG. 10 is a diagram showing an example of optical simulation in the optical unit according to the third embodiment of the present disclosure.

FIG. 9 is a diagram showing an example of optical simulation of an on-axis beam in an optical unit having no diaphragm. FIG. 10 is a diagram showing an example of optical simulation in the optical unit according to the third embodiment of the present disclosure. The conditions of the first lens 1 and the second lens 2A in FIGS. 9 and 10 are the same as those in FIG. 7.

The diameter $d_{4a}$ of the opening portion 4a of the diaphragm 4 was set to 40 μm.

There is a case where the optical unit 10B may be used, for example, in an optical system in which the NA is not determined by the optical system on the image side. In this case, when the beam diameter of the incident light is large, the optical performance will deteriorate due to the influence of the aberration of the first lens 1 and the second lens 2A.

For example, as shown in FIG. 9, when the beam diameter of a beam $f_4$ on the optical axis O is large, an image is blurred because the light having poor light-collecting performance even on the axis and far from the optical axis is incident.

In contrast, in the present embodiment, the diaphragm 4 restricts the beam diameter of the incident beam at each angle of view, which is incident on the first flat surface 1a.

In FIG. 10, beams $f_5$, $f_6$, and $f_7$ are parallel beams incident on the axis, at both angles of view of 40°, and at both angles of view of 80°. For example, the beam $f_5$ is excellently imaged on the image surface, as can be seen in comparison with the beam $f_4$ in FIG. 9. The same applies to the imaging states of the beams $f_6$ and $f_7$.

As described above, according to the optical unit 10B of the present embodiment, excellent optical performance can be obtained even with a smaller diameter, similarly to the second embodiment.

In particular, in the present embodiment, excellent optical performance can be obtained even when used in an apparatus having an optical system in which the NA is not determined on the image side.

Fourth Embodiment

An optical unit according to a fourth embodiment of the present disclosure will be described.

Figure 11:
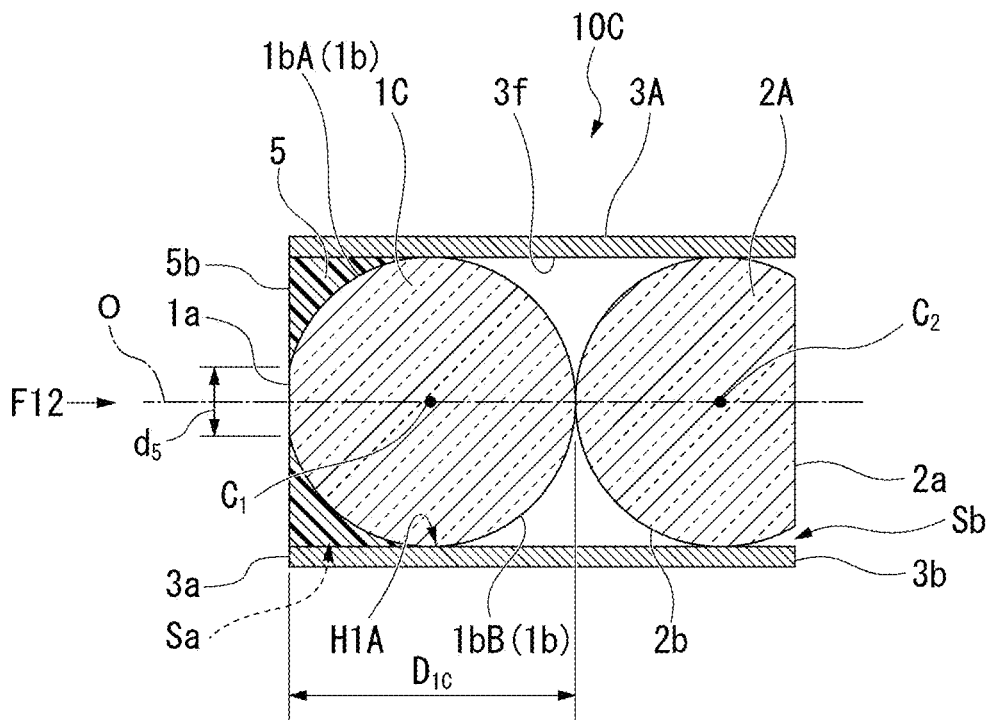
FIG. 11 is a schematic sectional view showing an example of an optical unit according to a fourth embodiment of the present disclosure.
Figure 12:
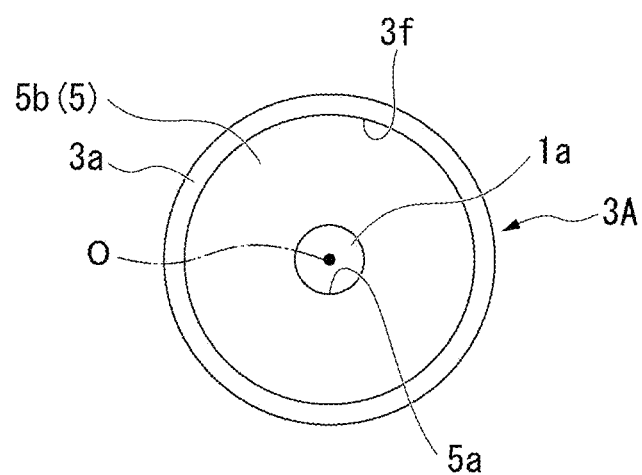
FIG. 12 is a side view of FIG. 11 as viewed from F12.

FIG. 11 is a schematic sectional view showing an example of the optical unit according to the fourth embodiment of the present disclosure. FIG. 12 is a side view of FIG. 11 as viewed from F12.

As shown in FIG. 11, an optical unit 10C of the present embodiment includes a first lens 1C instead of the first lens 1 in the optical unit 10A of the second embodiment, and further includes a resin portion 5 (diaphragm). Hereinafter, differences from the second embodiment will mainly be described.

Similar to the first lens 1, the first lens 1C is formed as a spherical segment of which a height $D_{1C}$ is larger than the radius $R_1$ of the first convex spherical surface 1b and smaller than twice the radius $R_2$ of the first convex spherical surface 1b. However, the size of the first flat surface 1a in the present embodiment matches the lens effective region. For this reason, $D_{1C}$ is larger than $D_1$ in the second embodiment.

Hereinafter, in the first convex spherical surface 1b, the first end portion 3a side of the first holding portion H1A is referred to as a first spherical portion 1bA, and the second lens 2A side of the first holding portion H1A is referred to as a second spherical portion 1bB.

The resin portion 5 is arranged between the first spherical portion 1bA and the inner peripheral surface 3f so as to cover the entire first spherical portion 1bA. The resin portion 5 extends to an outer peripheral portion of the first flat surface 1a. The resin portion 5 has a distal end surface 5b located on the same surface as the first flat surface 1a and the first end portion 3a outside the first flat surface 1a.

For this reason, as shown in FIG. 12, an opening portion 5a passing through the distal end surface 5b of the resin portion 5 is formed along the edge of the first flat surface 1a. The inner diameter of the opening portion 5a is $d_5$, which is the same as the diameter of the first flat surface 1a.

In the example shown in FIG. 11, the distal end surface 5b extends up to the inner peripheral surface 3f. The resin portion 5 shown in FIG. 11 is provided so as to fill the entire first space Sa between the first spherical portion 1bA and the inner peripheral surface 3f. However, a gap may be formed between the inner peripheral surface 3f and the resin portion 5 as long as the resin portion 5 covers at least the entire first spherical portion 1bA.

The material of the resin portion 5 contains a material having a light-absorbing property. For this reason, the resin portion 5 has a light-absorbing property. The lower the light transmittance of the resin portion 5, the more preferable. For example, the light transmittance of the resin portion 5 may be 0% or more and 10% or less. As materials having light-absorbing properties, light-absorbing materials such as carbon, dark coloring materials, black epoxy adhesives, black UV curable resins, and the like, are exemplary examples.

In the present embodiment, the resin portion 5 is formed by solidifying a resin material in which a light-absorbing material is dispersed. The resin material and the light-absorbing material used for the resin portion 5 are not particularly limited as long as these materials are materials that can be polished during the surface-polishing, which will be described below.

In particular, in a case where the resin material used for the resin portion 5 has a high fixing force with respect to the holding member 3A and the first spherical portion 1bA, the holding force of the resin portion 5 is also applied in addition to a frictional force generated at a contact portion between the first spherical portion 1bA and the inner peripheral surface 3f. Thus, the first lens 1 is more stably held by the holding member 3A.

Since the resin portion 5 in the present embodiment has a light-absorbing property, the resin portion 5 serves as a diaphragm with a diameter $d_5$. For this reason, particularly even when the resin portion 5 is used in an apparatus having an optical system in which the NA is not determined on the image side, excellent optical performance can be obtained.

Figure 13:
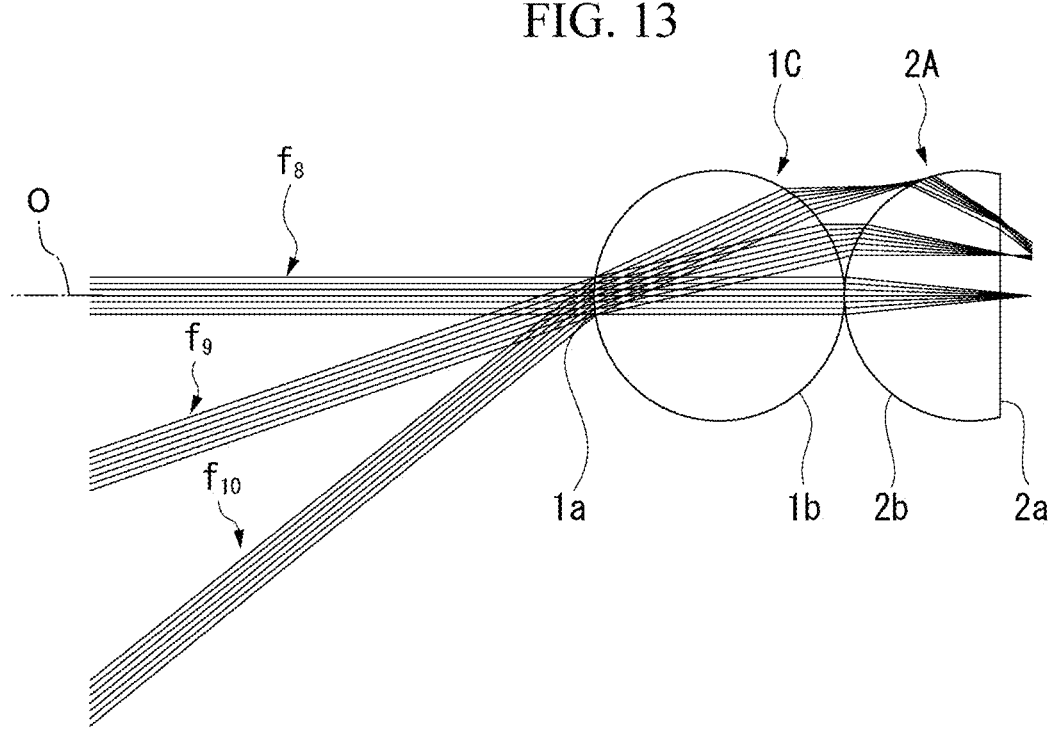
FIG. 13 is a diagram showing an example of optical simulation in the optical unit according to the fourth embodiment of the present disclosure.

FIG. 13 is a diagram showing an example of optical simulation in the optical unit according to the fourth embodiment of the present disclosure. The conditions of the second lens 2A in FIG. 13 are the same as those in FIGS. 7 and 10. The conditions of the first lens 1C are the same as those in FIG. 10, except that the height $D_{1C}$ of the spherical segment is set so as to have a $d_5$ of 60 μm.

In FIG. 13, beams $f_8$, $f_9$, and $f_{10}$ are parallel beams incident on the axis, at both angles of view of 40°, and at both angles of view of 80°.

According to FIG. 13, the beams $f_8$, $f_9$, and $f_{10}$ are excellently imaged on the image surface, substantially similar to the third embodiment.

Next, a method for manufacturing the optical unit 10C will be described.

Figure 14:
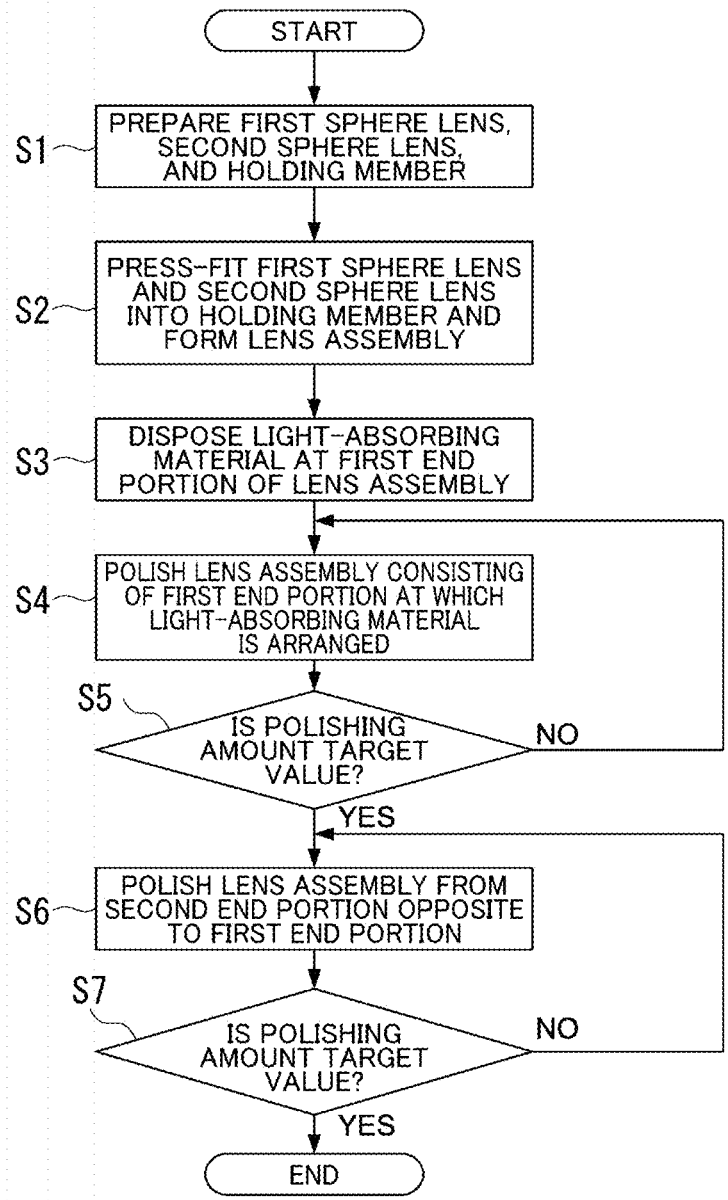
FIG. 14 is a flowchart showing an example of a method for manufacturing the optical unit according to the fourth embodiment of the present disclosure.

FIG. 14 is a flowchart showing an example of a method for manufacturing the optical unit according to the fourth embodiment of the present disclosure. FIGS. 15A to 15G are schematic diagrams illustrating examples of the method for manufacturing the optical unit according to the fourth embodiment of the present disclosure.

The optical unit 10C is manufactured, for example, by executing Steps S1 to S7 shown in FIG. 14 in accordance with a flow shown in FIG. 14.

In Step S1, a first sphere lens, a second sphere lens, and a holding member are prepared.

Figure 15A:
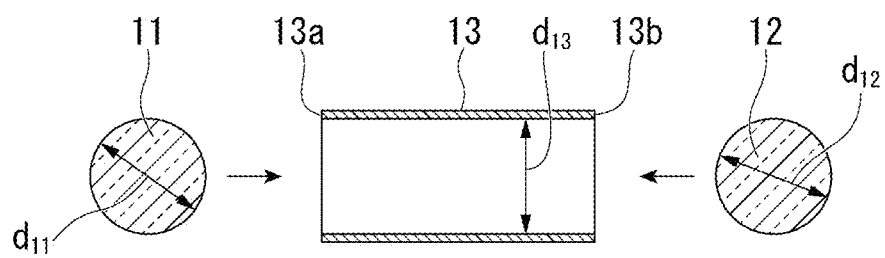
FIG. 15A is a schematic diagram illustrating an example of the method for manufacturing the optical unit according to the fourth embodiment of the present disclosure.

As shown in FIG. 15A, the first sphere lens 11 consists of a sphere with a diameter $d_{11}$. The second sphere lens 12 consists of a sphere with a diameter $d_{12}$.

The cylindrical member 13 is a holding member into which the first sphere lens 11 and the second sphere lens 12 can be press-fitted. The cylindrical member 13 has a shape in which the cylindrical portion 3h extends longer than the holding member 3A.

$d_{11}$ is twice $R_1$. $d_{12}$ is twice $R_2$. Assuming that the smaller one of $d_{11}$ and $d_{12}$ is $d_a$ and the larger one thereof is $d_b$, an inner diameter $d_{13}$ of the cylindrical member 13 is set within the range of $d_c$ in Formula (2).

After Step S1, Step S2 is performed.

In Step S2, the first sphere lens and the second sphere lens are press-fitted into the holding member to form a lens assembly.

Figure 15B:
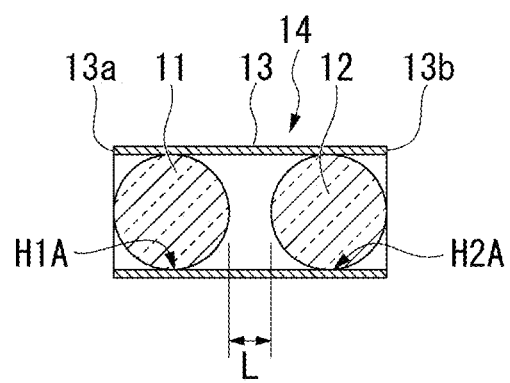
FIG. 15B is a schematic diagram illustrating an example of the method for manufacturing the optical unit according to the fourth embodiment of the present disclosure.

For example, as shown in FIG. 15B, the first sphere lens 11 and the second sphere lens 12 are press-fitted into both end portions of the cylindrical member 13 to form the lens assembly 14. In this case, the first sphere lens 11 and the second sphere lens 12 are inserted such that the inter-surface distance between the first convex spherical surface 1b and the second convex spherical surface 2b becomes L. L may satisfy Formula (1). L is 0 in the optical unit 10C of the present embodiment.

In the present embodiment, the first sphere lens 11 and the second sphere lens 12 are inserted inside a first end surface 13a (first end portion) and a second end surface 13b (second end portion) of the cylindrical member 13.

When the first sphere lens 11 and the second sphere lens 12 are press-fitted, the cylindrical member 13, which is the contact portions of the first sphere lens 11 and the second sphere lens 12, is deformed, and each of the first holding portion H1A and the second holding portion H2A is formed.

As described above, the lens assembly 14 is formed, and Step S2 is completed.

After Step S2, Step S3 is performed.

In Step S3, a light-absorbing material is arranged at the first end portion of the lens assembly.

Figure 15C:
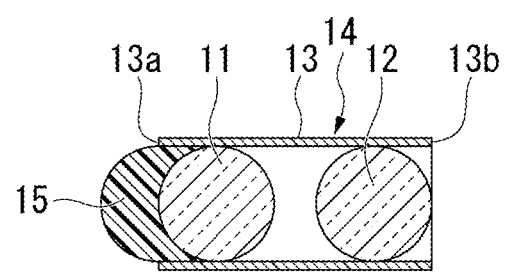
FIG. 15C is a schematic diagram illustrating an example of the method for manufacturing the optical unit according to the fourth embodiment of the present disclosure.

As shown in FIG. 15C, a light-absorbing resin 15 is applied to the surface of the first sphere lens 11 that faces the first end surface 13a. The light-absorbing resin 15 is a resin for forming the resin portion 5. For example, the light-absorbing resin 15 is formed by dispersing a light-absorbing material such as carbon in a base resin such as acrylic resin. As the base resin, for example, a thermosetting resin, an ultraviolet curable resin, or the like may be used.

The light-absorbing resin 15 is applied to the extent that the light-absorbing resin sticks out to the outside of the cylindrical member 13 beyond the first end surface 13a, and then solidified using curing means according to the base resin.

As described above, Step S3 is completed.

After Step S3, Step S4 is performed.

In Step S4, the lens assembly is polished from the second end portion opposite to the first end portion.

Figure 15D:
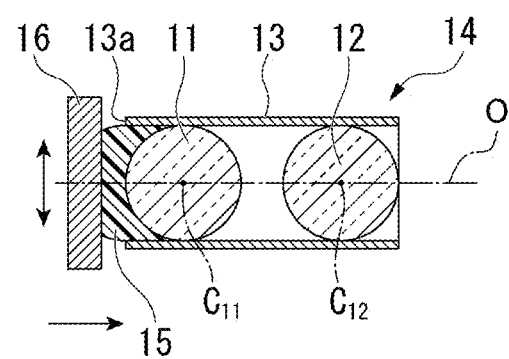
FIG. 15D is a schematic diagram illustrating an example of the method for manufacturing the optical unit according to the fourth embodiment of the present disclosure.

As shown in FIG. 15D, a polishing tool 16 starts polishing from the first end surface 13a. However, in the present embodiment, the light-absorbing resin 15 protruding more than the first end surface 13a is polished first. A polishing direction is a direction in which the first flat surface 1a is formed. In the present embodiment, for example, the polishing direction is a direction orthogonal to the optical axis O passing through the sphere center $C_{11}$ of the first sphere lens 11 and the sphere center $C_{12}$ of the second sphere lens 12.

When the first sphere lens 11 starts to be polished, the polishing tool 16 polishes the light-absorbing resin 15 and the cylindrical member 13 around the first sphere lens 11 together with the first sphere lens 11.

After the first sphere lens 11 is polished to some extent to form a flat surface at the end portion of the first sphere lens 11, Step S5 is performed.

In Step S5, whether or not the polishing amount of the first sphere lens 11 is a target value is determined.

In the present step, the polishing amount of the first sphere lens 11 is measured. A method for measuring the polishing amount is not particularly limited. Before the polishing amount is measured, the lens assembly 14 may be cleaned, as necessary.

Figure 15E:
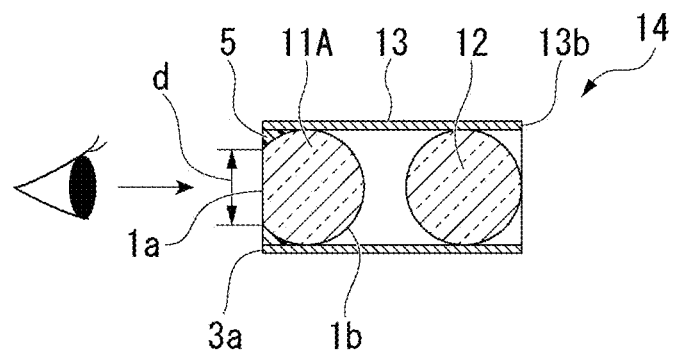
FIG. 15E is a schematic diagram illustrating an example of the method for manufacturing the optical unit according to the fourth embodiment of the present disclosure.

For example, as shown in FIG. 15E, the polishing processing may be stopped, and the diameter d of a flat surface formed on the first sphere lens 11 may be measured with a microscope or the like and converted into the polishing amount or the height of the spherical segment. According to this measurement, since the size of the first flat surface 1a and the size of the opening portion of the resin portion 5 can be directly measured, the size accuracy of the diaphragm of the optical unit 10C is easily improved.

For example, the fixed positions of the cylindrical member 13 and the first sphere lens 11 may be measured, and the polishing amount may be measured on the basis of a change in the length of the cylindrical member 13.

In a case where the polishing amount has not reached an allowable range of the target value, Step S4 is performed.

In a case where the polishing amount has reached the allowable range of the target value, Step S6 is performed.

Steps S4 and S5 constitute a first polishing step of surface-polishing the lens assembly from the first end portion into which the first sphere lens is press-fitted, and forming the first sphere lens in a spherical segment shape.

When the first polishing step is completed, the resin portion 5 and the first lens 1 are formed at the end portion of the lens assembly 14 opposite to the second end surface 13b.

In Step S6, the lens assembly is polished from the second end portion opposite to the first end portion.

Figure 15F:
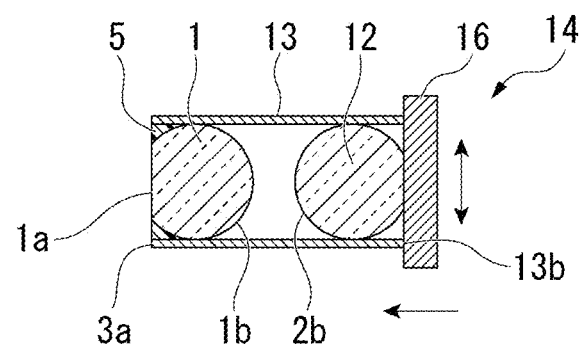
FIG. 15F is a schematic diagram illustrating an example of the method for manufacturing the optical unit according to the fourth embodiment of the present disclosure.

In the present step, as shown in FIG. 15F, polishing is performed from the second end surface 13b by the polishing tool 16.

After the second sphere lens 12 is polished to some extent to form a flat surface at the end portion of the second sphere lens 12, Step S7 is performed.

In Step S7, whether or not the polishing amount of the second sphere lens 12 is a target value is determined.

In the present step, the polishing amount of the second sphere lens 12 is measured. A method for measuring the polishing amount is not particularly limited. For example, a similar measurement method in Step S5 may be used.

Figure 15G:
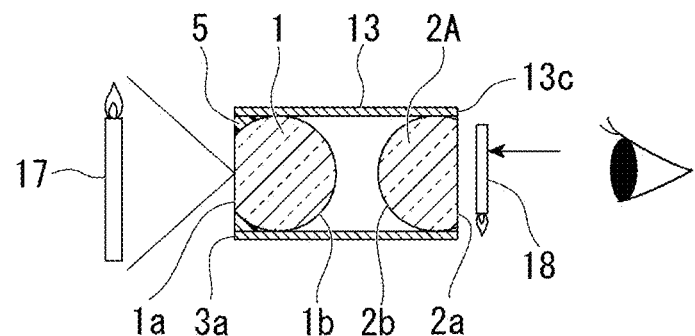
FIG. 15G is a schematic diagram illustrating an example of the method for manufacturing the optical unit according to the fourth embodiment of the present disclosure.

However, in the present step, the polishing amount may be substituted by the measurement of an image position. For example, as shown in FIG. 15G, the polishing processing is stopped, and an object 17 for measurement is arranged at a position with a predetermined observation distance from the first flat surface 1a. A measurer measures a relative position between the position of an image 18 of the object 17 and a polished end surface 13c of the cylindrical member 13 in an optical axis direction by using, for example, a focusing mechanism of a microscope, or the like.

In this case, it is possible to determine an appropriate polishing amount of the second sphere lens 12 including the optical performance of the first lens 1 formed in the first polishing step.

In a case where the polishing amount has not reached the allowable range of the target value, Step S6 is performed.

In a case where the polishing amount has reached the allowable range of the target value, Step S8 is performed.

Steps S6 and S7 constitute a second polishing step of surface-polishing the lens assembly from the second end portion into which the second sphere lens is press-fitted, and forming the second sphere lens in a spherical segment shape.

After the second polishing step is completed, the optical unit 10C as shown in FIG. 11 is manufactured.

In the optical unit 10C, the first lens 1 is arranged on the object side and the second lens 2 is arranged on the image side. Thus, in the above description, an example in which the first end portion of the lens assembly 14 is polished, and then, the second end portion is polished has been described. However, for example, in a case where the first lens 1 is arranged on the image side and the second lens 2 is arranged on the object side, and in a case where the polishing amount is not substituted by the measurement of the image position in Step S7, the execution order of Steps S4 and S5 and Steps S6 and S7 may be interchanged.

Although the method for manufacturing the optical unit 10C has been described above in detail, part of the above-described manufacturing method can be appropriately modified.

Figure 17:
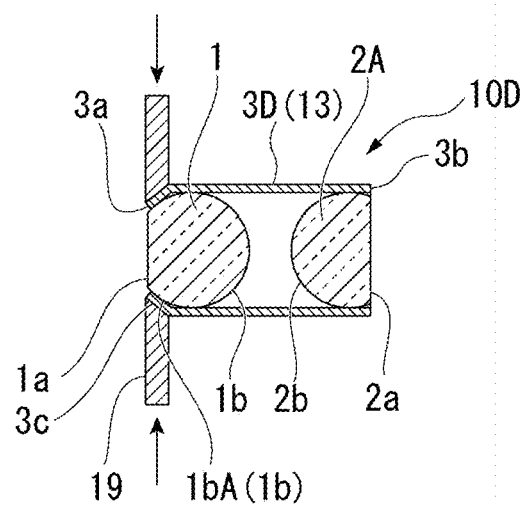
FIG. 17 is a schematic diagram illustrating the example of the method for manufacturing the optical unit according to the modification example of the fourth embodiment of the present disclosure.

FIG. 16 is a flowchart showing an example of a method for manufacturing an optical unit according to a modification example of the fourth embodiment of the present disclosure. FIG. 17 is a schematic diagram illustrating the example of the method for manufacturing the optical unit according to the modification example of the fourth embodiment of the present disclosure.

For example, in the modification example of the method for manufacturing the optical unit 10C, Steps S11 to S17 shown in FIG. 16 are executed in accordance with the flow shown in FIG. 16.

FIG. 17 shows an optical unit 10D manufactured in the modification example. The optical unit 10D has the diameter-reduced portion 3c instead of the resin portion 5 of the optical unit 10C. Hereinafter, differences from the fourth embodiment will mainly be described.

Steps S11 and S12 in the present modification example are the same as Steps S1 and S2 in the fourth embodiment.

After Step S12, Step S13 is performed.

Step S13 is the same as Step S4 except that the first end portion of the lens assembly 14 is polished in a state in which the light-absorbing resin 15 is not applied.

Steps S14 to S16 are the same as Steps S5 to S7.

Steps S13 and S14 constitute the first polishing step in the present modification example, and Steps S15 and S16 constitute the second polishing step in the present modification example.

After the completion of Step S16, the optical unit 10A as shown in FIG. 4 is formed.

In the present modification example, Step S17 is performed after Step S16.

In Step S17, the end portion processing of the lens assembly 14 after the completion of the polishing is performed.

For example, in a case where the diameter-reduced portion 3c is formed at the first end portion, as shown in FIG. 17, the cylindrical member 13 in the vicinity of the first end portion 3a is bent toward the first spherical portion 1bA by using a press tool 19. Accordingly, the optical unit 10D having a holding member 3D in which the diameter-reduced portion 3c is formed is manufactured. The diameter-reduced portion 3c covers the first spherical portion 1bA on the outer peripheral portion of the first flat surface 1a. The diameter-reduced portion 3c serves as a diaphragm because the diameter-reduced portion blocks light directed toward the first spherical portion 1bA.

The end portion processing in Step S17 is not limited to the formation of the diameter-reduced portion 3c. For example, in order to locate the first end portion 3a closer to the second lens 2A than the first flat surface 1a, the end portion processing may be performed to remove the cylindrical member 13 on the first end portion 3a side. As for the second end portion 3b, similarly, in order to locate the second end portion 3b closer to the first lens 1 than the second flat surface 2a, the end portion processing of removing the cylindrical member 13 on the second end portion 3b side may be performed.

For example, the end portion processing may be the processing of chamfering the corners formed between the first end portion 3a and the second end portion 3b, and the outer peripheral surface 3g.

For example, the end portion processing may be the processing of providing the diaphragm 4 at the end portion.

Fifth to Eighth Embodiments

Next, endoscopes according to fifth to eighth embodiments of the present disclosure will be described.

FIGS. 18A to 18D are sectional views showing examples of the endoscopes according to the fifth to eighth embodiments of the present disclosure.

An endoscope according to each embodiment includes an optical unit according to any of the above-described embodiments. Hereinafter, as an example, an example in a case where the optical unit 10A according to the second embodiment is provided will be described.

Figure 18A:
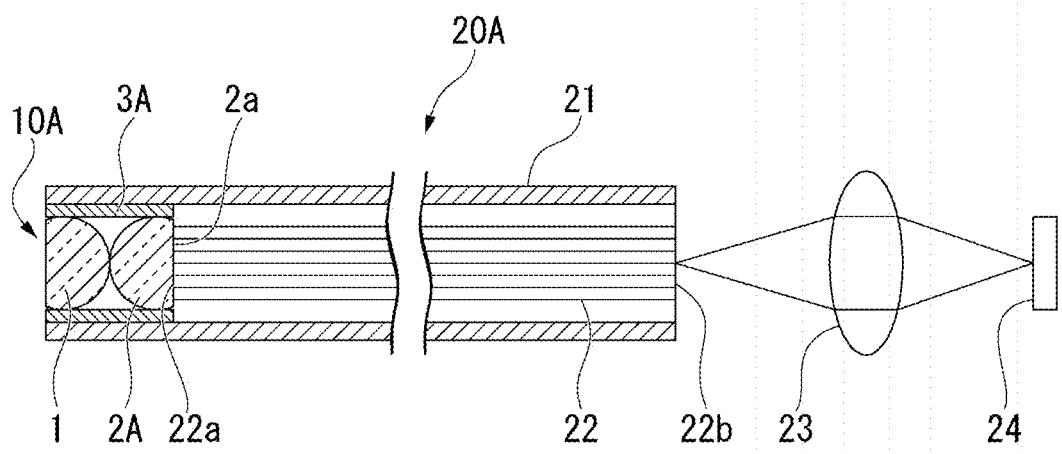
FIG. 18A is a sectional view showing an example of an endoscope according to a fifth embodiment of the present disclosure.

An endoscope 20A according to the fifth embodiment shown in FIG. 18A has an insertion part that is inserted into a subject. The optical unit 10A, a tubular member 21, a fiber bundle 22, an imaging lens 23, and an imaging element 24 are provided inside the insertion part.

The optical unit 10A in the present embodiment is used as an objective optical system in the endoscope 20A.

The tubular member 21 is a tube that fixes the holding member 3 of the optical unit 10A inside a distal end portion on the right side of the drawing.

The fiber bundle 22 is a bundle of a large number of optical fibers and transmits an image on an image surface of the optical unit 10A. The fiber bundle 22 is inserted inside the tubular member 21 such that a distal end surface 22a is located on the image surface of the optical unit 10A. A proximal surface 22b of the fiber bundle 22 is arranged at a proximal end of the tubular member 21.

The imaging lens 23 forms an image on the proximal surface 22b.

The imaging element 24 photoelectrically converts the image formed by the imaging lens 23 to form image signals. The imaging element 24 is connected to a display device (not shown) through a wiring line 25, and sends the image signals to the display device.

Accordingly, an image within the range of the field of view of the first lens 1 is displayed on the display device.

Figure 18B:
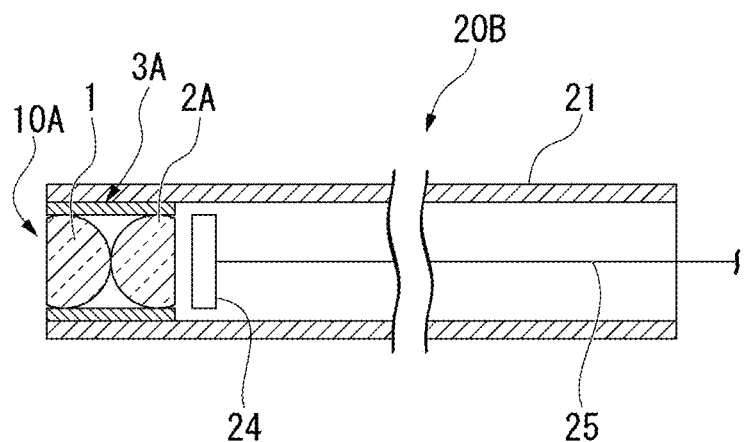
FIG. 18B is a sectional view showing an example of an endoscope according to a sixth embodiment of the present disclosure.

As shown in FIG. 18B, an endoscope 20B according to the sixth embodiment is configured by removing the fiber bundle 22 and the imaging lens 23 from the endoscope 20A according to the fifth embodiment.

In the present embodiment, the imaging element 24 is arranged on the image surface of the optical unit 10A inside the tubular member 21. The wiring line 25 is inserted through the tubular member 21 and extends from an opening at the proximal end of the tubular member 21 to the display device (not shown).

Figure 18C:
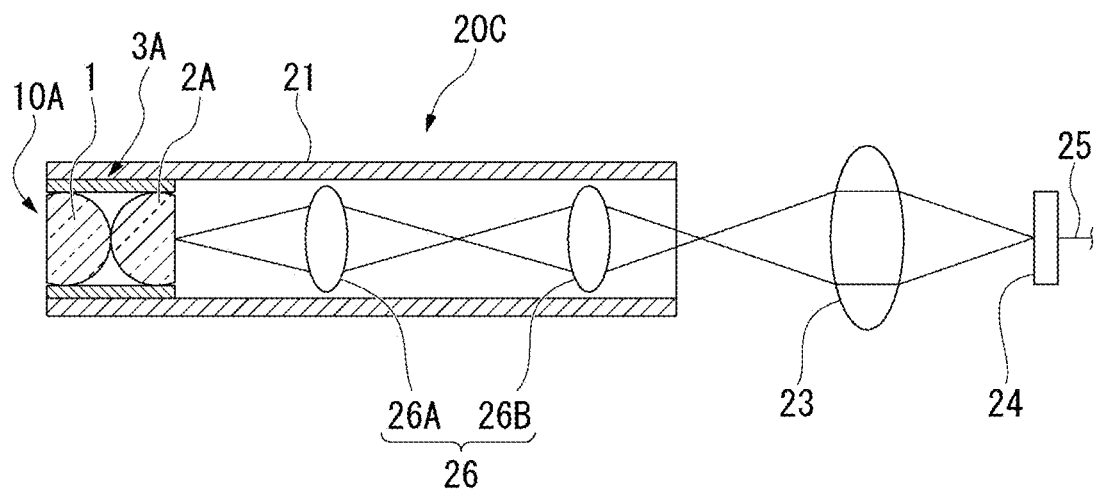
FIG. 18C is a sectional view showing an example of an endoscope according to a seventh embodiment of the present disclosure.

As shown in FIG. 18C, an endoscope 20C according to the seventh embodiment includes a relay optical system 26 instead of the fiber bundle 22 of the endoscope 20A according to the fifth embodiment.

The relay optical system 26 relays the image formed on the image surface of the optical unit 10A to an object surface of the imaging lens 23. For example, the relay optical system 26 includes relay lenses 26A and 26B. The types of relay lenses 26A and 26B are not particularly limited. For example, each of the relay lenses 26A and 26B may be a lens that refracts light on a lens surface, or a gradient index lens in which the refractive index changes in a radial direction.

The number of lenses in the relay optical system 26 is not particularly limited as long as two or more lenses are provided.

Figure 18D:
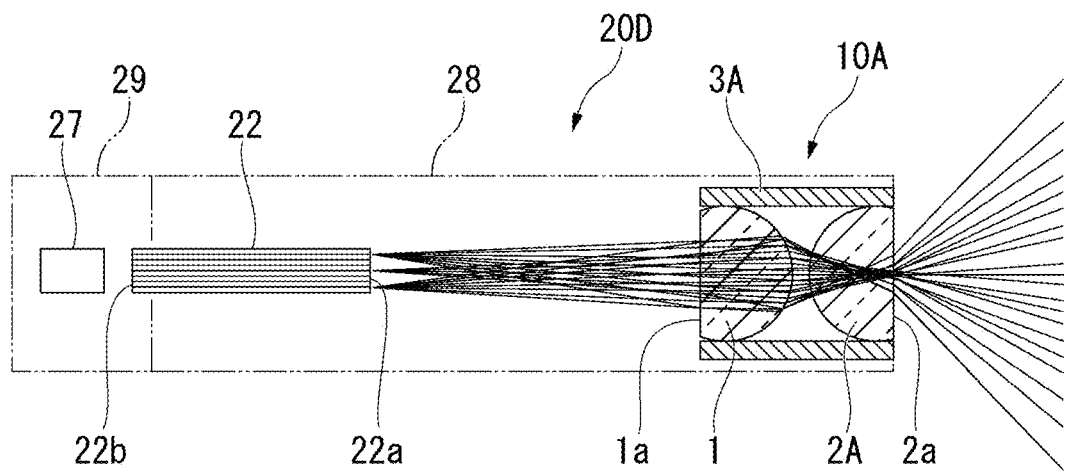
FIG. 18D is a sectional view showing an example of an endoscope according to an eighth embodiment of the present disclosure.

As shown in FIG. 18D, an endoscope 20D according to the eighth embodiment has an insertion part 28 that is inserted into the subject. The optical unit 10A and the fiber bundle 22 are arranged inside the insertion part 28. In the present embodiment, the fiber bundle 22 extends up to the proximal end of the insertion part 28 and is connected to a light source device 29. A light source 27 that generates illumination light is provided inside the light source device 29.

For example, an imaging optical system similar to the endoscopes 20A, 20B, and 20C according to the fifth to seventh embodiments may be arranged in the insertion part 28 of the present embodiment.

According to the endoscope 20D of the present embodiment, the illumination light emitted from the light source 27 is incident on the proximal surface 22b of the fiber bundle 22, guided by the fiber bundle 22, and emitted from the distal end surface 22a. The emitted light is incident on the first flat surface 1a, condensed by the first lens 1 and the second lens 2A, and then emitted to the outside of the second flat surface 2a. The emitted light spreads radially outward from a distal end portion of the insertion part 28 to illuminate the subject.

According to the endoscopes 20A, 20B, and 20C of the fifth to seventh embodiments, the imaging optical system is provided with the optical unit 10A. Thus, the diameter of the distal end portion of the insertion part can be reduced, and an excellent image of the subject can be acquired.

According to the endoscope 20D of the eighth embodiment, the illumination optical system is provided with the optical unit 10A. Thus, the diameter of the distal end portion of the insertion part 28 can be reduced, and the subject can be excellently identified.

Ninth Embodiment

A fiber scanning device according to a ninth embodiment of the present disclosure will be described.

Figure 19:
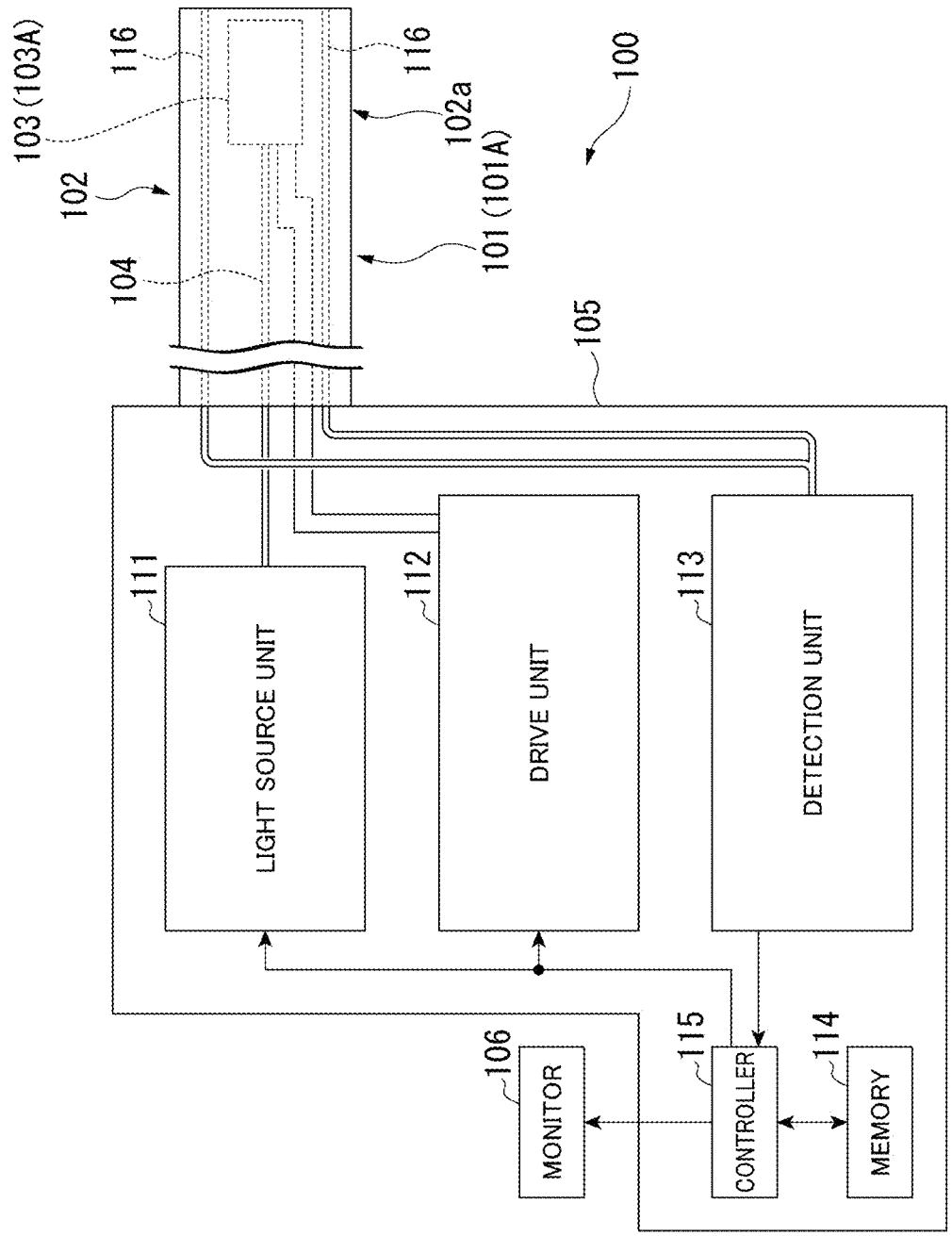
FIG. 19 is a schematic configuration diagram showing an example of a fiber scanning device according to a ninth embodiment of the present disclosure.
Figure 20:
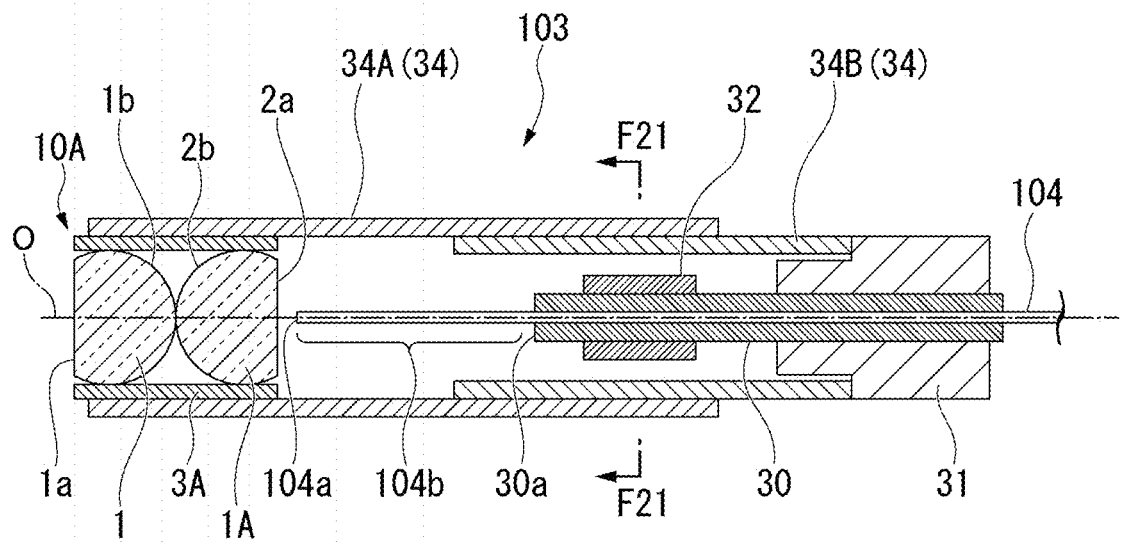
FIG. 20 is a schematic sectional view showing an example of the inside of an insertion part in the fiber scanning device according to the ninth embodiment of the present disclosure.
Figure 21:
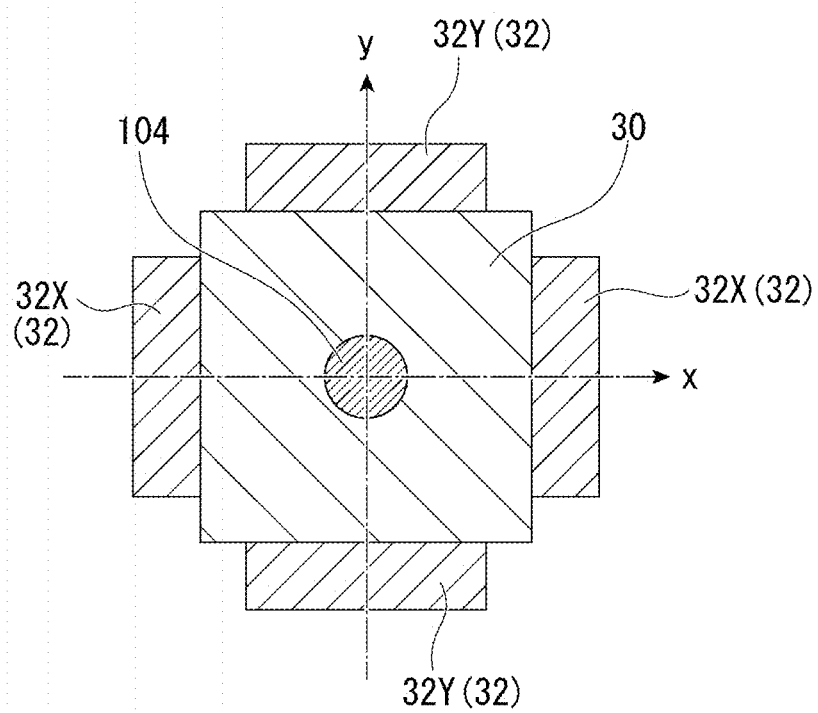
FIG. 21 is a schematic sectional view along line F21-F21 in FIG. 20.

FIG. 19 is a schematic configuration diagram showing an example of the fiber scanning device according to the ninth embodiment of the present disclosure. FIG. 20 is a schematic sectional view showing an example of the inside of an insertion part in the fiber scanning device according to the ninth embodiment of the present disclosure. FIG. 21 is a schematic sectional view along line F21-F21 in FIG. 20.

A scanning endoscope system 100 shown in FIG. 19 scans a subject with illumination light emitted from an optical fiber to acquire an image of the subject.

The scanning endoscope system 100 includes a scanning endoscope 101 (fiber scanning device), a main device body 105, and a monitor 106.

The scanning endoscope 101 has an insertion part 102 that can be inserted into the subject. The insertion part 102 is an elongated member having flexibility and has a distal end portion 102a at the distal end in an insertion direction.

An optical scanning unit 103 that scans the subject with illumination light, and a detection fiber 116 that guides return light from the subject are provided inside the distal end portion 102a.

As shown in FIG. 20, the optical scanning unit 103 has the optical unit 10A according to the second embodiment, an illumination fiber 104 (optical fiber), a ferrule 30 (holding material), a drive element 32, a support member 31, and a tubular member 34.

The illumination fiber 104 is an optical fiber that guides illumination light sent from the main device body 105, which will be described below. The illumination fiber 104 emits illumination light from an emission surface 104a provided at a distal end thereof. The NA at the emission surface 104a of the illumination fiber 104 is, for example, 0.25.

As shown in FIG. 19, the illumination fiber 104 extends from a proximal side of the optical scanning unit 103, and extends up to the main device body 105 connected to the proximal end of the insertion part 102 via the inside of the insertion part 102. A proximal end of the illumination fiber 104 is connected to a light source unit 111, which will be described below.

As shown in FIG. 20, the ferrule 30 surrounds the side surfaces of the illumination fiber 104 and extends in a longitudinal direction of the illumination fiber 104. The ferrule 30 holds a portion of the illumination fiber 104, including the emission surface 104a, closer to the proximal side than a distal end portion 104b inside the optical scanning unit 103.

As shown in the section orthogonal to the longitudinal direction in FIG. 21, the ferrule 30 is formed in a rod shape having a rectangular section. The illumination fiber 104 passes through a central portion of the rectangular section. The ferrule 30 is in close contact with the side surface of the illumination fiber 104.

As the materials of the ferrule 30, for example, zirconia (ceramic), nickel, and the like, are exemplary examples.

The drive element 32 is electrically connected to the main device body 105, which will be described below, and oscillates a distal end portion of the illumination fiber 104 on the basis of a control signal sent from the main device body 105. The configuration of the drive element 32 is not particularly limited as long as the distal end portion of the illumination fiber 104 can be oscillated.

In the example shown in FIG. 21, the drive element 32 consists of two piezoelectric elements 32X and two piezoelectric elements 32Y.

Each piezoelectric element 32X is joined to each of the side surfaces of the ferrule 30 facing each other in an x direction, which is a direction orthogonal to the longitudinal direction.

Each piezoelectric element 32Y is joined to each of the side surfaces of the ferrule 30 facing each other in a y direction, which is a direction orthogonal to the longitudinal direction and the x direction.

As shown in FIG. 20, the support member 31 supports the ferrule 30 closer to the proximal end than a position where the drive element 32 is arranged. For example, the support member 31 is formed in a substantially columnar shape, and has a proximal portion of the ferrule 30 fixed to a central portion thereof.

The tubular member 34 extends in the longitudinal direction of the illumination fiber 104. The tubular member 34 accommodates the illumination fiber 104 and the drive element 32 therein. A gap that allows the distal end portion 104b to oscillate is provided between the distal end portion 104b of the illumination fiber 104 and an inner surface of the tubular member 34.

In the present embodiment, the tubular member 34 has a first tubular member 34A and a second tubular member 34B.

The first tubular member 34A and the second tubular member 34B are coupled to each other such that the internal spaces thereof communicate with each other in the longitudinal direction. For example, in the example shown in FIG. 20, the second tubular member 34B and the first tubular member 34A are coupled to each other in a state in which a distal end portion of the second tubular member 34B is fitted to the inside of a proximal portion of the first tubular member 34A.

The optical unit 10A is fixed to the inside of a distal end portion of the first tubular member 34A. The optical axis O of the optical unit 10A is coaxial with a central axis of the first tubular member 34A.

A distal end portion of the support member 31 is fixed to the inside of a proximal portion of the second tubular member 34B.

In the optical scanning unit 103, the distal end portion 104b of the illumination fiber 104 is arranged coaxially with the optical axis O in a case where the ferrule 30 is in a straight state. The emission surface 104a is arranged on the image surface of the optical unit 10A.

For example, the optical scanning unit 103 may be manufactured as follows.

The support member 31 is brought into a state where the support member 31 supports the ferrule 30 including the illumination fiber 104 and is fixed to the proximal portion of the second tubular member 34B. The optical unit 10A is fixed to the distal end portion of the first tubular member 34A.

After that, the proximal portion of the first tubular member 34A and the distal end portion of the second tubular member 34B are coupled to each other. In this case, by adjusting a coupling position in the axial direction between the first tubular member 34A and the second tubular member 34B, it is possible to adjust the position of the emission surface 104a with respect to the image surface of the optical unit 10A.

The detection fiber 116 consists of an optical fiber inserted into the insertion part 102. The detection fiber 116 may be a fiber bundle having a plurality of optical fibers.

The distal end of the detection fiber 116 is formed with an incident surface on which return light is incident. The incident surface is arranged at the distal end of the distal end portion 102a.

A proximal end of the detection fiber 116 is formed with an emission surface through which the return light guided into the detection fiber 116 is emitted. The emission surface is arranged such that the return light can be emitted toward a detection unit 113 of the main device body 105, which will be described below.

As shown in FIG. 19, the main device body 105 includes the light source unit 111, the drive unit 112, the detection unit 113, a controller 115, and a memory 114.

The light source unit 111 generates illumination light. The configuration of the light source unit 111 is not particularly limited. For example, the light source unit 111 may have light sources that generate light in respective wavelength ranges of red (R), green (G), and blue (B), and a multiplexer that multiplexes the light. The light source unit 111 makes illumination light incident on the proximal end of the illumination fiber 104.

The drive unit 112 is electrically connected to the drive element 32 and the controller 115. The drive unit 112 drives the drive element 32 depending on a control signal sent from the controller 115.

In the present embodiment, the drive unit 112 applies a voltage corresponding to the drive amount to each piezoelectric element 32X and each piezoelectric element 32Y to expand and contract each element. For example, the ferrule 30 is curved in the x direction by relatively changing the length of each piezoelectric element 32X in the longitudinal direction. Similarly, the ferrule 30 is curved in the y direction by relatively changing the length of each piezoelectric element 32Y in the longitudinal direction.

The distal end portion 104b oscillates depending on the curving amount and curving direction of the ferrule 30.

The detection unit 113 receives the return light emitted from the emission surface of the detection fiber 116 and photoelectrically converts the return light. A detection signal generated by the photoelectric conversion is sent to the controller 115.

The detection unit 113 includes, for example, a demultiplexer that demultiplexes the return light into an R component, a G component, and a B component, and may have a detector that detects each of the demultiplexed light components, and an A/D converter that A/D converts the detection output of the detector.

The controller 115 controls the operation in the optical scanning unit 103. The controller 115 is electrically connected to the light source unit 111, the drive unit 112, the detection unit 113, the memory 114, and the monitor 106.

The controller 115 sends a control signal to the light source unit 111 to control ON and OFF of the illumination light.

The controller 115 sends a control signal to the drive unit 112 to control the operation of the drive element 32. For example, the controller 115 drives the drive element 32 such that the emission surface 104a moves spirally about the optical axis O. The controller 115 generates the data of the scanning position of the illumination light on the basis of the data of the drive amount.

The controller 115 causes the detection signal from the detection unit 113 and the data of the scanning position of the illumination light when the detection signal is received to be stored in the memory 114.

The controller 115 generates image data based on the detection signal and the data of the scanning position stored in the memory 114 and sends the image data to the monitor 106.

The monitor 106 displays the image data sent from controller 115.

The operation of the scanning endoscope 101 will be described.

Figure 22:
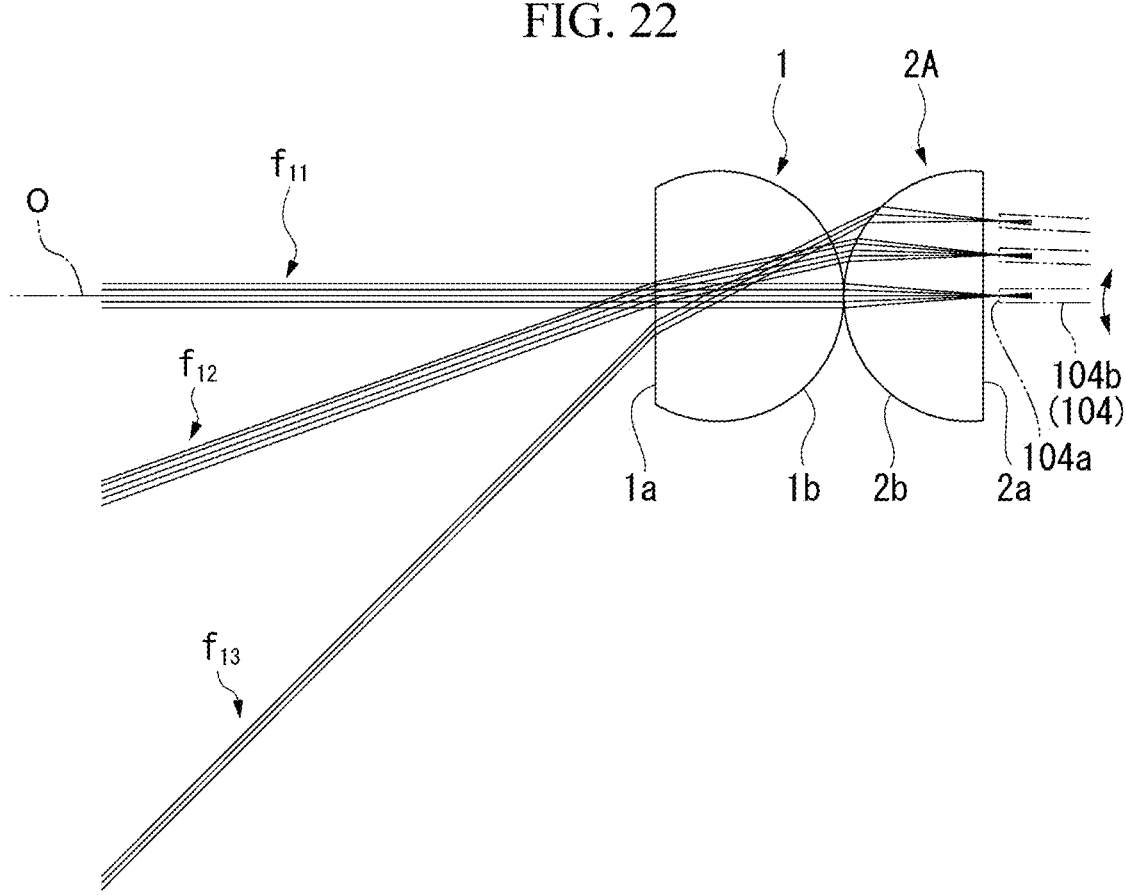
FIG. 22 is a diagram showing an example of optical simulation of irradiation light in the fiber scanning device according to the ninth embodiment of the present disclosure.

FIG. 22 is a diagram showing an example of optical simulation of irradiation light in the fiber scanning device according to the ninth embodiment of the present disclosure.

According to the scanning endoscope 101, the illumination light can be emitted from the emission surface 104a while the distal end portion 104b of the illumination fiber 104 is oscillated. For example, the controller 115 drives the drive element 32 such that the emission surface 104a draws a spiral trajectory. For example, as shown in FIG. 22, when the distal end portion 104b oscillates within a plane shown in the drawing, the image height of the emission position of the illumination light changes.

For example, the distal end portion 104b in a straight state emits the illumination light guided by the illumination fiber 104 from the emission surface 104a on the optical axis O. In this case, as shown as a beam $f_{11}$, the illumination light is condensed by the second lens 2A and the first lens 1 and emitted as a parallel beam from the first flat surface 1a.

For example, when the distal end portion 104b moves upward in the drawing, as the image height of the emission surface 104a increases, a scanning beam in which the scanning angle of view on a side opposite to the movement direction of the distal end portion 104b increases is formed like beams $f_{12}$, $f_{13}$, and the like.

In the example shown in FIG. 22, both angles of view of the beams $f_{12}$, $f_{13}$, and the like are 40° and 80°, respectively.

Even when the optical unit 10A used in the present embodiment has a small diameter, it is possible to perform wide-angle illumination light scanning with both angles of view of about 80°. In that case, like the illumination fiber 104, in an NA of about 0.25, as shown in FIG. 22, the illumination light is hardly diffused because there is little influence of aberration. For this reason, illumination light suitable for excellent scanning illumination is formed.

For this reason, the diameter of the scanning endoscope 101 including the optical unit 10A can be reduced.

Tenth Embodiment

A fiber scanning device according to a tenth embodiment of the present disclosure will now be described.

A scanning endoscope 101A (fiber scanning device) of the present embodiment shown in FIG. 19 includes an optical scanning unit 103A instead of the optical scanning unit 103 of the ninth embodiment.

The scanning endoscope 101A can be used for the scanning endoscope system 100 instead of the scanning endoscope 101. Hereinafter, differences from the ninth embodiment will mainly be described.

Figure 23:
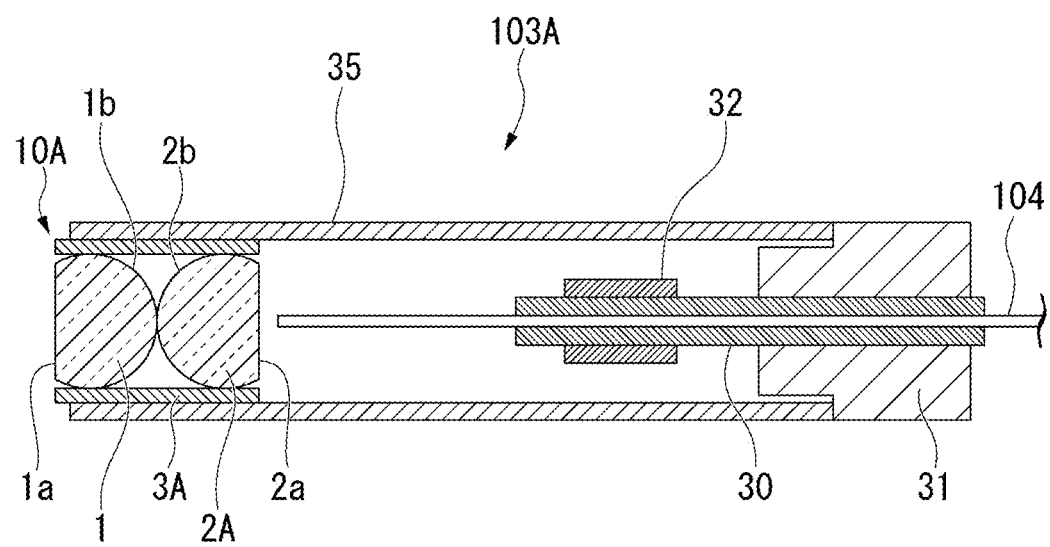
FIG. 23 is a schematic sectional view showing an example of the inside of an insertion part in a fiber scanning device according to a tenth embodiment of the present disclosure.

FIG. 23 is a schematic sectional view showing an example of the inside of an insertion part in the fiber scanning device according to the tenth embodiment of the present disclosure.

As shown in FIG. 23, the scanning endoscope 101A includes a tubular member 35 instead of the tubular member 34 in the ninth embodiment.

The tubular member 35 is a member similar to the tubular member 34 except that the tubular member 35 is formed of a single pipe.

The tubular member 35 may be fixed first to either the support member 31 or the optical unit 10A. In a case where the position of the emission surface 104a with respect to the image surface of the optical unit 10A is adjusted, the position of a member to be fixed later has only to be adjusted.

The tubular member 35 may have a fixing portion that fixes the optical unit 10A and the support member 31 in a positioned state. In this case, the position of the emission surface 104a with respect to the image surface of the optical unit 10A is determined depending on the axial distance of each fixed portion.

According to the scanning endoscope 101A of the present embodiment, similarly to the ninth embodiment, the optical unit 10A is provided. Thus, the diameter can be reduced. In particular, since the tubular member 35 is made of a single pipe, the diameter can be made even smaller than in the ninth embodiment.

In addition, in each of the above embodiments, an example in which the holding member is formed of a cylindrical member has been mainly described. However, in a case where the outer diameters of the first lens and the second lens are different from each other, the holding member may be formed of a tubular member of which the inner diameter changes continuously or stepwise. In this case, even when the outer diameters of the first lens and the second lens are different from each other, the press-fit margins can be made equal to each other.

In each of the above embodiments, an example in which the first lens and the second lens are press-fitted into the holding member has been described. However, as long as the holding member can hold the first lens and the second lens with a frictional force, the method of assembling the first lens and the second lens is not limited to the press-fitting. For example, methods may be used, such as the shrink fitting of inserting the first lens and the second lens in a state where the holding member is thermally expanded and then cooling the first and second lenses to reduce the diameter of the holding member and the crimping of inserting the first lens and the second lens into the holding member having a larger diameter than the first lens and the second lens and then pressing the holding member.

In the above third embodiment, an example in which the diaphragm is formed of a plate member has been described. However, the diaphragm may be formed, for example, by applying a light-absorbing resin on the first flat surface of the first lens.

In the above third and fourth embodiments, an example in which the diaphragm is provided closer to the object side or closer to the outer peripheral portion of the first lens than the first lens on the object side has been described. However, the diaphragm may be provided closer to the image side or the outer peripheral portion of the second lens than the second lens on the image side.

In the above third embodiment, an example in a case where the resin portion 5 serves as a diaphragm has been described. However, the resin portion 5 may be formed of a transparent material. In this case, the resin portion 5 does not have a diaphragm function, but has a function to prevent polishing powder from entering the first space Sa when the first lens 1 is polished.

For example, in a case where the resin portion is not arranged in the first space Sa, there is a concern that the polishing powder may adhere to the first flat surface 1a after drying if the polishing powder that has clogged the first space Sa is not removed during cleaning.

In contrast, when the resin portion 5 is arranged in the entire first space Sa, the polishing powder can be easily removed simply by being washed away from on the distal end surface 5b. For this reason, after the polishing, a step of removing the polishing powder that has entered the first space Sa is unnecessary.

Even in a case where the resin portion 5 is arranged in a part of the first space Sa, the amount by which the polishing powder is clogged is reduced compared to a case where the resin portion 5 is not arranged. Thus, the polishing powder can be easily removed.

In the description of the above fifth to tenth embodiments, an example in which the endoscope or the fiber scanning device includes the optical unit 10A according to the second embodiment has been described. However, instead of the optical unit 10A, the optical units according to the first, third, and fourth embodiments, and modification examples of the fourth embodiment may be provided.

Although the respective preferred embodiments and modification examples of the present disclosure have been described above, the present disclosure is not limited to such embodiments and modification examples. Additions, omissions, substitutions, and other changes of configurations are possible without departing from the scope of the present disclosure.

Additionally, the present disclosure is not limited by the foregoing description, but only by the scope of the appended claims.

What is claimed is:

1. An optical unit comprising:
   a first lens configured to be formed in a spherical segment having a first flat surface and a first convex spherical surface;
   a second lens configured to be formed in a spherical segment having a second flat surface and a second convex spherical surface; and a holding member configured to have a first end portion that surrounds the first lens and a second end portion that surrounds the second lens, wherein the holding member holds the first lens and the second lens with a frictional force such that the first convex spherical surface and the second convex spherical surface are adjacent to each other between the first end portion and the second end portion, the first end portion is located on the same surface as the first flat surface or closer to the second lens than the first flat surface, the second end portion is located on the same surface as the second flat surface or closer to the first lens than the second flat surface; and a height of the spherical segment of the first lens is larger than a radius of the first convex spherical surface and less than twice the radius of the first convex spherical surface and a height of the spherical segment of the second lens is larger than a radius of the second convex spherical surface and less than twice the radius of the second convex spherical surface, or a height of the spherical segment of the first lens is larger than a radius of the first convex spherical surface and less than twice the radius of the first convex spherical surface or a height of the spherical segment of the second lens is larger than a radius of the second convex spherical surface and less than twice the radius of the second convex spherical surface.

2. An optical unit comprising:

a first lens configured to be formed in a spherical segment having a first flat surface and a first convex spherical surface;

a second lens configured to be formed in a spherical segment having a second flat surface and a second convex spherical surface; and a holding member configured to have a first end portion that surrounds the first lens and a second end portion that surrounds the second lens, wherein the holding member holds the first lens and the second lens with a frictional force such that the first convex spherical surface and the second convex spherical surface are adjacent to each other between the first end portion and the second end portion, the first end portion is located on the same surface as the first flat surface or closer to the second lens than the first flat surface, the second end portion is located on the same surface as the second flat surface or closer to the first lens than the second flat surface; and the first flat surface is non-perpendicular to an axis connecting a sphere center of the first convex spherical surface and a sphere center of the second convex spherical surface.

3. An optical unit comprising:

a first lens configured to be formed in a spherical segment having a first flat surface and a first convex spherical surface;

a second lens configured to be formed in a spherical segment having a second flat surface and a second convex spherical surface; and a holding member configured to have a first end portion that surrounds the first lens and a second end portion that surrounds the second lens, wherein the holding member holds the first lens and the second lens with a frictional force such that the first convex spherical surface and the second convex spherical surface are adjacent to each other between the first end portion and the second end portion, the first end portion is located on the same surface as the first flat surface or closer to the second lens than the first flat surface, the second end portion is located on the same surface as the second flat surface or closer to the first lens than the second flat surface; and when a radius of the first convex spherical surface is $R_1$, a radius of the second convex spherical surface is $R_2$, a refractive index of the second lens is n2, and an inter-surface distance between the first lens and the second lens is L, the following Formula (1) is satisfied

[Formula 1]

$$L \leq (R_1 + R_2)\left(\frac{n_2}{\sqrt{n_2^2 - 1}} - 1\right). \quad (1)$$

4. The optical unit according to claim 1, wherein the holding member is a tube having a circular section, and when a smaller one of a diameter of the first lens and a diameter of the second lens is da, and a larger one thereof is db, and an inner diameter of the holding member between the first lens and the second lens is dc, the following Formula (2) is satisfied

[Formula 2]

$$0.8 d_b < d_c \leq d_a \quad (2).$$

5. The optical unit according to claim 1, wherein the first end portion is located on the same surface as the first flat surface and the second end portion is located on the same surface as the second flat surface.

6. An optical unit comprising:

a first lens configured to be formed in a spherical segment having a first flat surface and a first convex spherical surface;

a second lens configured to be formed in a spherical segment having a second flat surface and a second convex spherical surface; and a holding member configured to have a first end portion that surrounds the first lens and a second end portion that surrounds the second lens, wherein the holding member holds the first lens and the second lens with a frictional force such that the first convex spherical surface and the second convex spherical surface are adjacent to each other between the first end portion and the second end portion, the first end portion is located on the same surface as the first flat surface or closer to the second lens than the first flat surface, the second end portion is located on the same surface as the second flat surface or closer to the first lens than the second flat surface; and wherein a refractive index of the first lens is $n_1$, a radius of the first convex spherical surface is $R_1$, a refractive index of the second lens is $n_2$, a radius of the second convex spherical surface is $R_2$, and a height of the spherical segment of the second lens is $D_2$, and an inter-surface distance between the first convex spherical surface and the second convex spherical surface is L, the following Formula (3) is satisfied

[Formula 3]

$$D_2 \leq \frac{n_2\{R_2L(1-n_1)+R_1R_2\}}{R_1(n_2-1)+L(n_2-1)(1-n_1)+R_2(n_1-1)}. \quad (3)$$

7. An optical unit comprising:
a first lens configured to be formed in a spherical segment having a first flat surface and a first convex spherical surface;
a second lens configured to be formed in a spherical segment having a second flat surface and a second convex spherical surface; and
a holding member configured to have a first end portion that surrounds the first lens and a second end portion that surrounds the second lens,
wherein the holding member holds the first lens and the second lens with a frictional force such that the first convex spherical surface and the second convex spherical surface are adjacent to each other between the first end portion and the second end portion,
the first end portion is located on the same surface as the first flat surface or closer to the second lens than the first flat surface,
the second end portion is located on the same surface as the second flat surface or closer to the first lens than the second flat surface; and
a first holding portion that holds the first lens and a second holding portion that holds the second lens are formed on an inner surface of the holding member, and
when a space between the first holding portion and the first end portion and between the first lens and the inner surface is defined as a first space, and a space between the second holding portion and the second end portion and between the second lens and the inner surface is defined as a second space, a resin portion is further provided in which resin is arranged in one or both of the first space and the second space.

8. The optical unit according to claim 7, wherein the resin portion includes a material having a light-absorbing property and forms a diaphragm close to one or both edges of the first flat surface and the second flat surface.

9. The optical unit according to claim 1, further comprising:
a diaphragm that is arranged on the first flat surface or at a position farther from the second lens than the first lens and restricts a diameter of a beam transmitted through the first flat surface.

10. The optical unit according to claim 1, wherein the first convex spherical surface and the second convex spherical surface are in contact with each other.

11. The optical unit according to claim 1, wherein the first lens is press-fitted into the holding member, and the second lens is press-fitted into the holding member.

12. A fiber scanning device comprising:
the optical unit according to claim 1;
an optical fiber configured to guide light incident from a proximal end and emit the light from a distal end; and
a drive element configured to oscillate a distal end portion of the optical fiber including the distal end.

13. The fiber scanning device according to claim 12, further comprising:
a holding material configured to hold the optical fiber;
a support member configured to support the holding material closer to the proximal end than a position where the drive element is arranged; and
a tubular member configured to be fixed to the support member in a state in which the optical fiber and the drive element are accommodated inside with a gap that allows the distal end portion to oscillate,
wherein the drive element is provided at an outer peripheral portion of the holding material, and
the optical unit is fixed to the tubular member such that the light emitted from the distal end of the optical fiber is incident thereon.

14. The fiber scanning device according to claim 13,
wherein the tubular member has a first tubular member and a second tubular member coupled to each other such that internal spaces of the first and second tubular members communicate with each other in a longitudinal direction,
the optical unit is fixed to the first tubular member, and
the support member is fixed to the second tubular member.

15. A method for manufacturing an optical unit, comprising:
preparing a first sphere lens, a second sphere lens, and a holding member that allows the first sphere lens and the second sphere lens to be press-fitted thereinto, and press-pressing the first sphere lens and the second sphere lens into an inside of the holding member to form a lens assembly;
first surface-polishing the lens assembly from a first end portion into which the first sphere lens is press-fitted to form the first sphere lens in a spherical segment shape; and
second surface-polishing the lens assembly from a second end portion into which the second sphere lens is press-fitted to form the second sphere lens in a spherical segment shape.

16. The method for manufacturing an optical unit according to claim 15, further comprising:
disposing a light-absorbing material between an inner surface of the holding member and the first sphere lens from the first end portion after the lens assembly is formed and before the first surface-polishing is started; and
in the first surface-polishing, the light-absorbing material is also surface-polished when the first sphere lens is polished.

17. The method for manufacturing an optical unit according to claim 15, further comprising:
bending an end portion of the holding member surrounding the first sphere lens toward a spherical surface of the first sphere lens after the first surface-polishing.

18. The method for manufacturing an optical unit according to claim 15, further comprising:
a first determining whether or not a polishing amount of the first sphere lens is a target value after the first surface-polishing.

19. The method for manufacturing an optical unit according to claim 15, wherein
the forming of the lens assembly further includes
inserting the first sphere lens and the second lens into the holding member such that the following Formula (1) is satisfied when a radius of the first sphere lens is $R_1$, a radius of the second spherical surface is $R_2$, a refractive index of the second lens is n2, and an inter-surface distance between the first lens and the second lens is L

[Formula 1]

$$L \le (R_1 + R_2)\left(\frac{n_2}{\sqrt{n_2^2 - 1}} - 1\right). \quad (1)$$

* * * * *